(12) United States Patent  
Barnhouse et al.

(10) Patent No.: US 8,696,672 B2
(45) Date of Patent: Apr. 15, 2014

(54) ABRADING TOOL FOR PREPARING INTERVERTEBRAL DISC SPACES

(75) Inventors: Michael P. Barnhouse, Wilmington, NC (US); Scott Hill, Southport, NC (US)

(73) Assignee: Baxano Surgical, Inc., Raleigh, NC (US)

( * ) Notice: Subject to any disclaimer, the term of this patent is extended or adjusted under 35 U.S.C. 154(b) by 940 days.

(21) Appl. No.: 12/692,159

(22) Filed: Jan. 22, 2010

(65) Prior Publication Data

US 2011/0184420 A1    Jul. 28, 2011

(51) Int. Cl.
*A61B 17/00* (2006.01)
(52) U.S. Cl.
USPC .............................. 606/79; 606/85
(58) Field of Classification Search
USPC ............................. 606/79–85, 86 R
See application file for complete search history.

(56) References Cited

U.S. PATENT DOCUMENTS

| | | |
|---|---|---|
| 1,092,914 A | 4/1914 | Jones |
| 1,388,547 A | 8/1921 | Burns |
| 1,638,807 A | 8/1927 | Hopwood |
| 2,513,663 A | 7/1950 | McDaniel |
| 2,730,101 A | 1/1956 | Hoffman |
| 3,367,326 A | 2/1968 | Frazier et al. |
| 3,670,732 A | 6/1972 | Robinson |
| 4,046,144 A | 9/1977 | McFarlane |
| 5,030,201 A | 7/1991 | Palestrant |
| 5,100,402 A | 3/1992 | Fan |
| 5,197,962 A | 3/1993 | Sansom |
| 5,231,910 A | 8/1993 | Harsh et al. |
| 5,376,094 A | 12/1994 | Kline |
| 5,376,100 A | 12/1994 | Lefebvre |
| 5,591,170 A | 1/1997 | Spievack et al. |
| 5,607,440 A | 3/1997 | Danks |
| 5,693,011 A | 12/1997 | Onik |
| 5,709,697 A | 1/1998 | Ratcliff et al. |
| 5,746,745 A | 5/1998 | Abele |
| 5,787,591 A | 8/1998 | Lu ................................. 30/355 |
| 5,857,999 A | 1/1999 | Quick |
| 5,928,239 A | 7/1999 | Mirza |
| 5,935,143 A | 8/1999 | Hood ............................ 606/169 |
| 5,937,524 A | 8/1999 | Hornsby |
| 5,979,056 A | 11/1999 | Andrews |
| 6,159,179 A | 12/2000 | Simonson |
| 6,383,188 B2 | 5/2002 | Kuslich et al. |
| 6,389,699 B1 | 5/2002 | Ecer |
| 6,440,138 B1 | 8/2002 | Reiley et al. |
| 6,574,868 B1 | 6/2003 | Overholt ........................ 30/155 |
| 6,740,090 B1 | 5/2004 | Cragg et al. |
| 6,740,106 B2 | 5/2004 | Kobayashi |

(Continued)

OTHER PUBLICATIONS

International Search Report and Written Opinion From Corresponding PCT Application No. PCT/US2010/060406, Apr. 19, 2011 (14 pgs).

*Primary Examiner* — Matthew Lawson
(74) *Attorney, Agent, or Firm* — Kevin E. Flynn; Flynn IP Law

(57) ABSTRACT

Tools and methods for preparing an intervertebral disc space with an emphasis on abrading the vertebral endplates to promote controlled bleeding of the vertebral endplate without compromising the structural integrity of the vertebral endplate. Mechanisms to statically or dynamically alter blade angle of the cutter blade. Cutter blades may come in a variety of configurations including cutter blades with abrading heads for preparing endplates. Abrading heads may be used on upcutters or down cutters. A cutter assembly adapted to resist unwanted changes in blade angle.

22 Claims, 29 Drawing Sheets

(56) References Cited

U.S. PATENT DOCUMENTS

| | | |
|---|---|---|
| 6,746,451 B2 | 6/2004 | Middleton et al. |
| 6,863,672 B2 | 3/2005 | Reileyv |
| 7,172,611 B2 | 2/2007 | Harding |
| 7,500,977 B2 | 3/2009 | Assell |
| 7,588,574 B2 | 9/2009 | Assell |
| 7,632,274 B2 | 12/2009 | Assell |
| 7,931,689 B2 | 4/2011 | Hochschuler |
| 7,938,830 B2 | 5/2011 | Saadat |
| 8,052,613 B2 | 11/2011 | Assell |
| 2002/0016604 A1 | 2/2002 | Boock et al. ................ 606/159 |
| 2002/0188299 A1 | 12/2002 | Reiley et al. |
| 2003/0205024 A1 | 11/2003 | Pelton ......................... 52/786.1 |
| 2004/0215343 A1 | 10/2004 | Hochschuler et al. |
| 2005/0113836 A1 | 5/2005 | Lozier et al. ................... 606/80 |
| 2005/0113838 A1* | 5/2005 | Phillips et al. ................. 606/80 |
| 2005/0137612 A1 | 6/2005 | Assell |
| 2005/0149034 A1 | 7/2005 | Assell |
| 2005/0165406 A1 | 7/2005 | Assell et al. ................... 606/86 |
| 2005/0228420 A1 | 10/2005 | Harding et al. .............. 606/167 |
| 2005/0230510 A1 | 10/2005 | Flanhardt |
| 2005/0257660 A1 | 11/2005 | Hayden .......................... 83/846 |
| 2006/0241629 A1 | 10/2006 | Krebs et al. .................... 606/80 |
| 2007/0078483 A1* | 4/2007 | Ewaschuk et al. ........... 606/205 |
| 2007/0213735 A1 | 9/2007 | Saadat et al. ................... 606/79 |
| 2007/0260270 A1 | 11/2007 | Assell |
| 2007/0265652 A1 | 11/2007 | Assell et al. ................. 606/170 |
| 2008/0033466 A1 | 2/2008 | Assell |
| 2008/0269754 A1 | 10/2008 | Lutz |

* cited by examiner

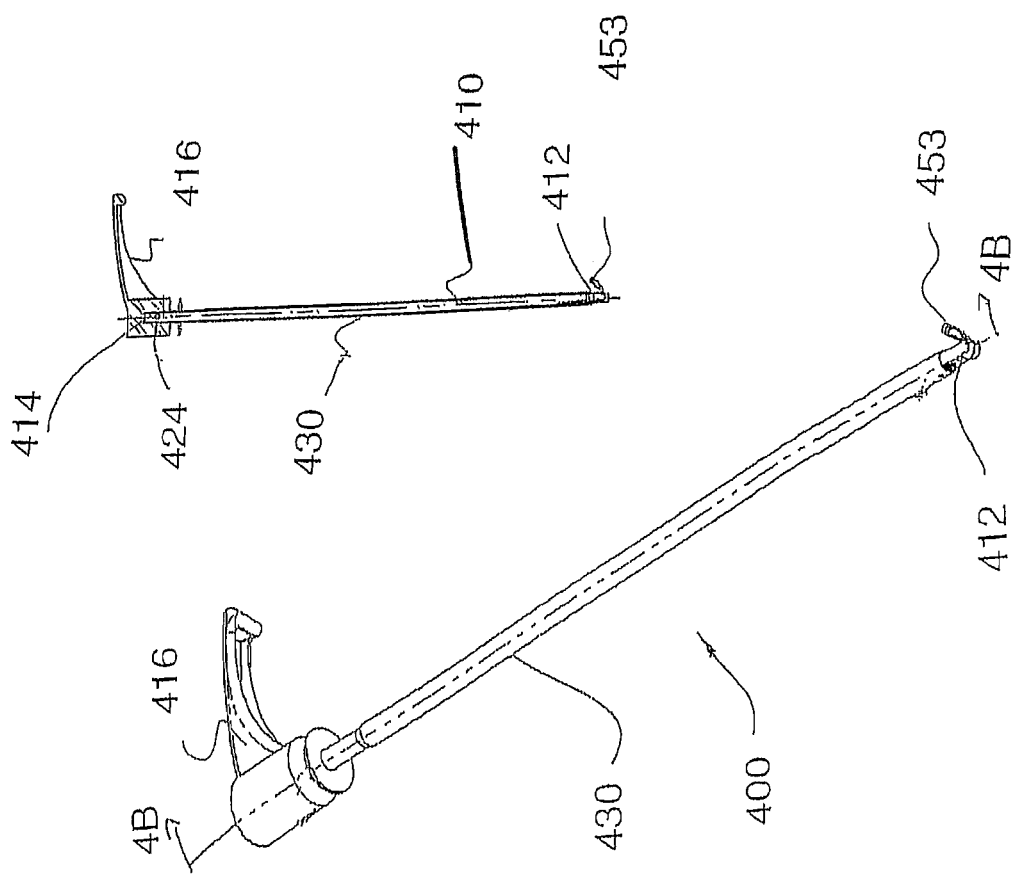

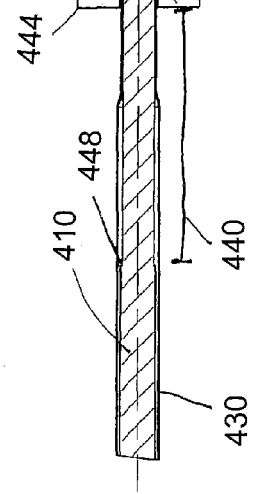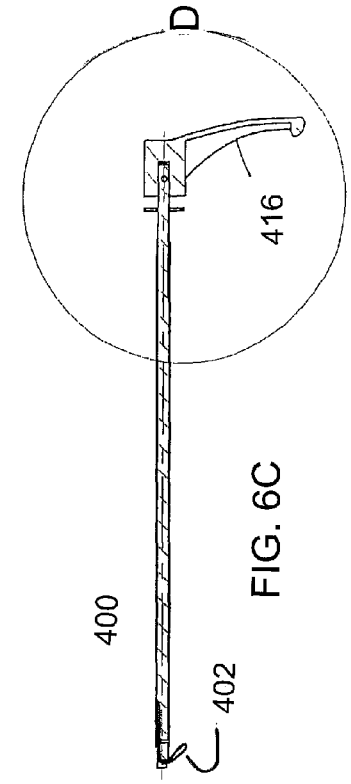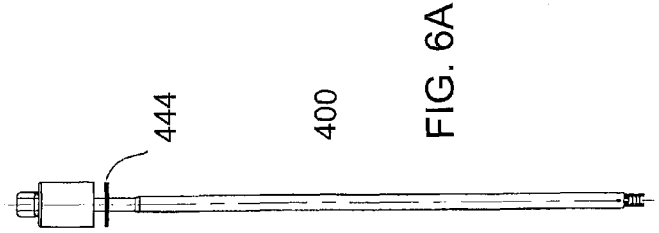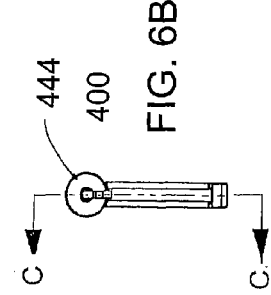
FIG. 6A
FIG. 6B
FIG. 6C
FIG. 6D

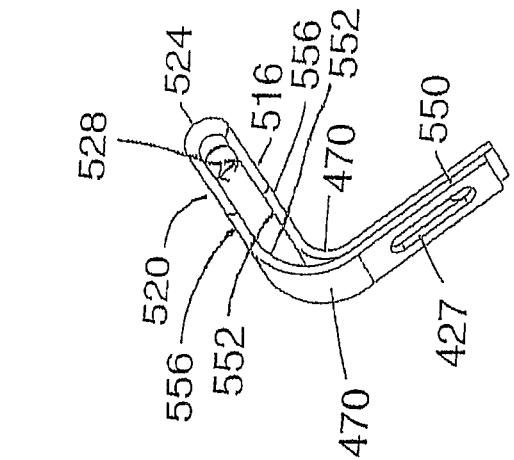
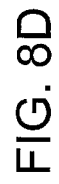
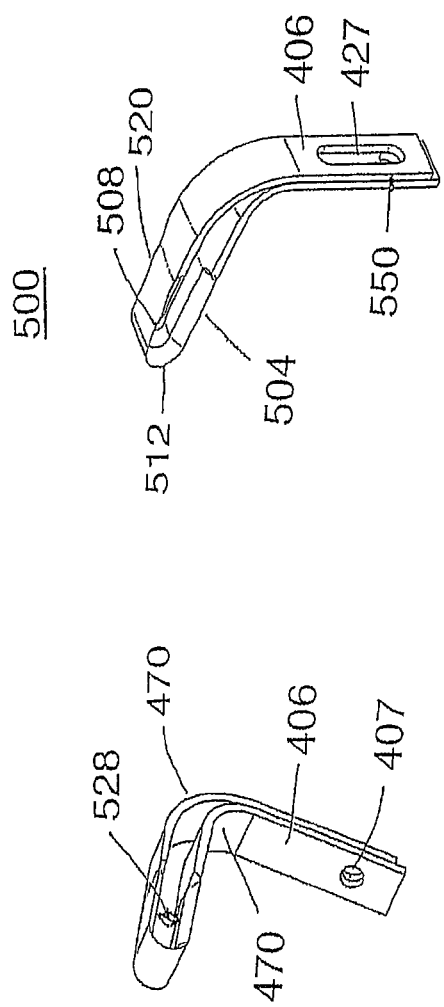
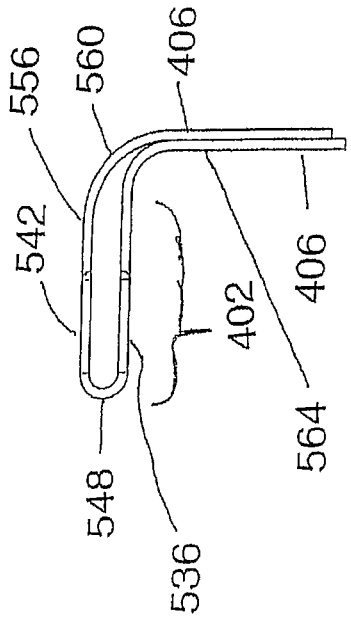

| 3010 | Deliver the sheathed abrading blade |
| --- | --- |

↓

| 3020 | Unsheathe the sheathed abrading blade |
| --- | --- |

↓

| 3030 | Capture the abrading blade within the radial slot portion of the sheath slot |
| --- | --- |

↓

| 3040 | Use abrading blade |
| --- | --- |

↓

| 3050 | Release abrading blade from the radial slot portion of the sheath slot |
| --- | --- |

↓

| 3060 | Sheathe the abrading blade |
| --- | --- |

↓

| 3070 | Withdraw the sheathed abrading blade |
| --- | --- |

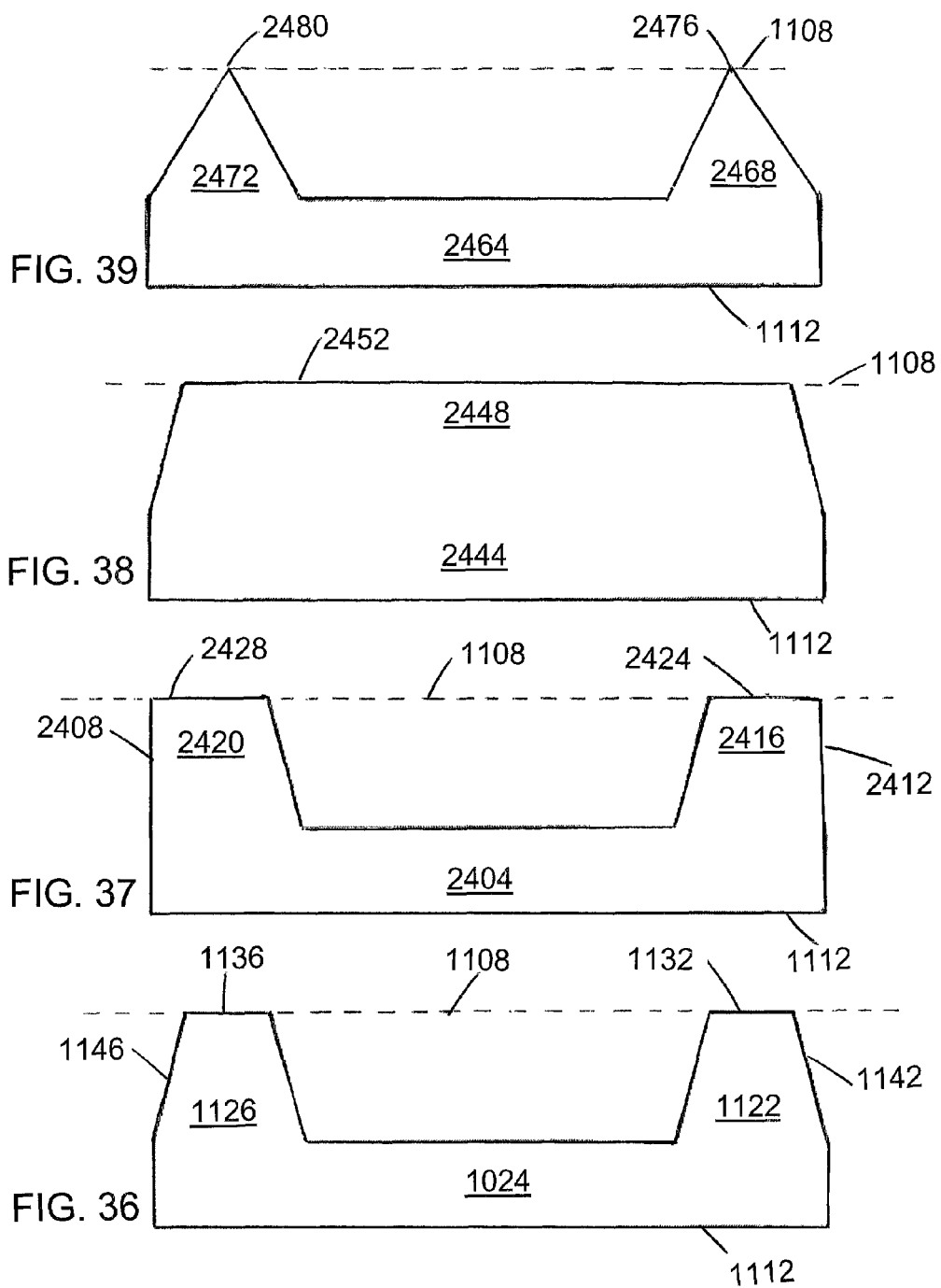

ABRADING TOOL FOR PREPARING INTERVERTEBRAL DISC SPACES

FIELD OF THE DISCLOSURE

This disclosure relates generally to improved tools and methods for preparing treatment sites within the spine, such as within the intervertebral space between two adjacent vertebral bodies for subsequent therapeutic procedures including therapies to promote fusion of the two adjacent vertebral bodies.

OVERVIEW

The present invention is an extension of work in a series of patent applications (now issued patents) with a common assignee. Relevant earlier work including general description of methods and tools for accessing the lower spine may be found in the following issued U.S. Patents: U.S. Pat. No. 6,575,979 issued Jun. 10, 2003 for Method and Apparatus for Providing Posterior or Anterior Trans-Sacral Access to Spinal Vertebrae; U.S. Pat. No. 7,087,058 issued Aug. 8, 2006 for Method and Apparatus for Providing Posterior or Anterior Trans-Sacral Access to Spinal Vertebrae; U.S. Pat. No. 6,558,386 issued May 6, 2003 for Axial Spinal Implant and Method and Apparatus for Implanting an Axial Spinal Implant Within the Vertebrae of the Spine; U.S. Pat. No. 6,740,090 issued May 25, 2004 for Methods and Apparatus for Forming Shaped Axial Bores Through Spinal Vertebrae; U.S. Pat. No. 6,790,210 issued Sep. 14, 2004 for Methods and Apparatus for Forming Curved Axial Bores Through Spinal Vertebrae; U.S. Pat. No. 6,558,390 issued May 6, 2003 for Methods and Apparatus for Performing Therapeutic Procedures in the Spine; U.S. Pat. No. 7,014,633 issued Mar. 21, 2006 for Methods of Performing Procedures in the Spine; U.S. Pat. No. 6,899,716 issued May 31, 2005 for Method and Apparatus for Spinal Augmentation; U.S. Pat. No. 6,921,403 issued Jul. 26, 2005 for Method and Apparatus for Spinal Distraction and Fusion; U.S. Pat. No. 7,309,338 issued Dec. 18, 2007 for Methods and Apparatus for Performing Therapeutic Procedures in the Spine; U.S. Pat. No. 7,329,259 issued Feb. 12, 2008 for Articulating Spinal Implant; U.S. Pat. No. 7,473,256 issued Jan. 6, 2009 for Method and Apparatus for Spinal Distraction; U.S. Pat. No. 7,491,236 issued Feb. 17, 2009 for Dual Anchor Prosthetic Nucleus Apparatus; U.S. Pat. No. 7,500,977 issued Mar. 10, 2009 for Method and Apparatus for Manipulating Tissue in the Spine; U.S. Pat. No. 7,530,993 issued May 12, 2009 for Method for Guiding Instrumentation Through Soft Tissue to a Point on the Spine; U.S. Pat. No. 7,547,317 issued Jun. 16, 2009 for Methods of Performing Procedures in the Spine; U.S. Pat. No. 7,547,324 issued Jun. 16, 2009 for Spinal Mobility Preservation Apparatus Having an Expandable Membrane; U.S. Pat. No. 7,569,056 issued Aug. 4, 2009 for Methods and Apparatus for Forming Shaped Axial Bores Through Spinal Vertebrae; U.S. Pat. No. 7,588,574 issued Sep. 15, 2009 for Kits for Enabling Axial Access and Procedures in the Spine; U.S. Pat. No. 7,601,171 issued Oct. 13, 2009 for Spinal Motion Preservation Assemblies; U.S. Pat. No. 7,608,077 issued Oct. 27, 2009 for Method and Apparatus for Spinal Distraction and Fusion; and U.S. Pat. No. 7,641,657 issued Jan. 5, 2010 for Method and Apparatus for Providing Posterior or Anterior Trans-Sacral Access to Spinal Vertebrae. These applications are incorporated by reference in their entirety.

Much of the work is described in great detail in the many applications referenced above and incorporated by reference into this application. Accordingly, the background of the invention provided here does not repeat all of the detail provided in the earlier applications, but instead highlights how the present invention adds to this body of work.

The spinal column is a complex system of bone segments (vertebral bodies and other bone segments) which are in most cases separated from one another by discs in the intervertebral spaces (sacral vertebrae are an exception). FIG. 1 shows the various segments of a human spinal column as viewed from the side. In the context of the present disclosure, a "motion segment" includes adjacent vertebrae, i.e., an inferior and a superior vertebral body, and the intervertebral disc space separating said two vertebral bodies, whether denucleated space or with intact or damaged spinal discs. Unless previously fused (or damaged), each motion segment contributes to the overall flexibility of the spine to flex to provide support for the movement of the trunk and head.

The vertebrae of the spinal cord are conventionally subdivided into several sections. Moving from the head to the tailbone, the sections are cervical 104, thoracic 108, lumbar 112, sacral 116, and coccygeal 120. The individual vertebral bodies within the sections are identified by number starting at the vertebral body closest to the head. The trans-sacral approach is well suited for access to vertebral bodies in the lumbar section and the sacral section. As the various vertebral bodies in the sacral section are usually fused together in adults, it is sufficient and perhaps more descriptive to merely refer to the sacrum rather than the individual sacral components.

The individual motion segments within the spinal columns allow movement within constrained limits and provide protection for the spinal cord. The discs are important to cushion and distribute the large forces that pass through the spinal column as a person walks, bends, lifts, or otherwise moves. Unfortunately, for a number of reasons referenced below, for some people, one or more discs in the spinal column will not operate as intended. The reasons for disc problems range from a congenital defect, disease, injury, or degeneration attributable to aging. Often when the discs are not operating properly, the gap between adjacent vertebral bodies is reduced and this causes additional problems including pain.

A range of therapies have been developed to alleviate the pain associated with spinal dysfunction. One class of solutions fuses the two adjacent vertebral bodies together with a permanent but inflexible spacing, also referred to as static stabilization or as spinal fusion.

TERMINOLOGY

It is useful to set forth some of the standard medical vocabulary before getting into a more detailed discussion of the background of the present invention. In the context of the this discussion: anterior refers to in front of the spinal column; (ventral) and posterior refers to behind the column (dorsal); cephalad means towards the patient's head (sometimes "superior"); caudal (sometimes "inferior") refers to the direction or location that is closer to the feet. As the present application contemplates accessing the various vertebral bodies and intervertebral spaces through a preferred approach that comes in from the sacrum and moves towards the head, proximal and distal are defined in context of this channel of approach. Consequently, proximal is closer to the beginning of the channel and thus towards the patient's feet or the surgeon, distal is further from the beginning of the channel and thus towards the patient's head, or more distant from the surgeon. When referencing tools including cutters or other tools to prepare the intervertebral disc space, distal would be the end intended for insertion into the access channel and proximal refers to the other end, generally the end closer to the handle for the tool.

In the context of this application, an upcutter with respect to a trans-sacral route for preparation of a disc is used to prepare the superior aspect of the disc, including possibly the inferior endplate of the adjacent distal vertebra. In the context of this application, a down cutter with respect to a trans-sacral route for preparation of a disc is used to prepare the inferior aspect of the disc, including possibly the superior endplate of the adjacent proximal vertebra. In the context of this application, a tool is an upcutter or down cutter independent of the blade angle of the tool.

The Operation of the Spine.

The bodies of successive lumbar, thoracic and cervical vertebrae articulate with one another and are separated by the intervertebral spinal discs. Each spinal disc includes a fibrous cartilage shell enclosing a central mass, the "nucleus pulposus" (or "nucleus" herein) that provides for cushioning and dampening of compressive forces to the spinal column. The shell enclosing the nucleus includes cartilaginous endplates adhered to the opposed cortical bone endplates of the cephalad and caudal vertebral bodies and the "annulus fibrosus" (or "annulus" herein) includes multiple layers of opposing collagen fibers running circumferentially around the nucleus pulposus and connecting the cartilaginous endplates. The nucleus is relatively inelastic, but the annulus can bulge outwardly slightly to accommodate loads axially applied to the spinal motion segment.

The intervertebral discs are anterior to the spinal canal and located between the opposed end faces or endplates of a cephalad vertebral body and a caudal vertebral body. The inferior articular processes articulate with the superior articular processes of the next succeeding vertebra in the caudal (i.e., towards the feet or inferior) direction. Several ligaments (supraspinous, interspinous, anterior and posterior longitudinal, and the ligamenta flava) hold the vertebrae in position yet permit a limited degree of movement. The assembly of two vertebral bodies, the interposed, intervertebral, spinal disc and the attached ligaments, muscles and facet joints is referred to as a "spinal motion segment".

The relatively large vertebral bodies located in the anterior portion of the spine and the intervertebral discs provide the majority of the weight bearing support of the vertebral column. Each vertebral body has relatively strong, cortical bone layer forming the exposed outside surface of the body, including the endplates, and weaker, cancellous bone in the center of the vertebral body.

Preparation of an Intervertebral Disc Space for Fusion.

Preparation of an intervertebral disc space for fusion can be described as a process of removing some or all the contents of the nucleus and the preparation of the endplates. This disclosure has a focus on the removal of nucleus material near the endplates and the preparation of the endplates. One process to prepare a motion segment for fusion therapy includes the removal of cartilage on the endplate in a manner that promotes bleeding that subsequently enhances bone growth and thus fusion. While the tools set forth in this disclosure are useful for particular processes for preparing the endplates for fusion, there are other processes that would use different tools that are also believed to be effective in preparing a disc space for fusion.

Design of tools for endplate preparation includes considerations in many cases of the efficiency with which the tool prepares the endplate.

SUMMARY OF THE DISCLOSURE

Disclosed herein are tool assemblies for use with tool heads with a number of components, and at least some of the components use shape memory materials. The tool head may be deployed in the interior of an intervertebral disc space and rotated relative to a central axis of the tool assembly which is substantially aligned with a centerline of an axis channel. Rotation of a tool head as part of a tool assembly within an intervertebral disc space abrades the material present there to remove it from the relevant vertebral endplate and to disrupt underlying vascular tissue. Tool heads with different attributes (such as throw length, head angle, and type) may be used in sequence to achieve objectives within the intervertebral disc space.

Disclosed herein are tools and methods for preparing an intervertebral disc space with an emphasis on abrading the vertebral endplates to promote controlled bleeding of the vertebral endplate without compromising the structural integrity of the vertebral endplate. The abrading process may be used to remove cartilage from the vertebral endplate if this remains to be done. Various mechanisms are discussed to either statically or dynamically alter blade angle of the cutter blade. Cutter blades may come in a variety of configurations including cutter blades with abrading heads for preparing endplates. Abrading heads may be used on upcutters or down cutters. Also disclosed is a cutter assembly adapted to resist unwanted changes in blade angle.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE FIGURES

The invention can be better understood with reference to the following figures. The components in the figures are not necessarily to scale, emphasis instead being placed upon illustrating the principles of the invention. Moreover, in the figures, like reference numerals designate corresponding parts throughout the different views.

FIGS. 4A-4B are views of a cutter assembly.

FIG. 6A-6D provide additional views of a cutter assembly including stops that limit the range of travel of the cutter sheath.

FIGS. 8A-8D show a series views of a closed loop cutter blade that is adapted to scrape away the cartilaginous endplate and roughen the vascularized endplate of the vertebral body so as to cause bleeding.

FIG. 32 is a flow chart of a process to use a sheath slot to resist changes to blade angle from contact with a proximal surface.

FIG. 36 repeats an end view of abrading head 1024 as described in FIG. 18.

FIG. 37 shows and end view of an abrading head 2404 with substantially perpendicular faces.

FIG. 38 shows an end view of an abrading head 2444 with a single rail.

FIG. 39 shows an end view of an abrading head 2464 that has a pair of rails with saw tooth profiles.

DETAILED DESCRIPTION

While the inventive tool assemblies described below may be used in other surgical procedures, it is useful in context to describe how these tools could be adapted for use in a trans-sacral approach. As noted above there are many advantages associated with a minimally invasive, low trauma trans-sacral axial approach. The trans-sacral axial approach (described and disclosed in commonly assigned United States Patents referenced above) has a number of advantages over other routes for delivery of therapeutic devices to motion segments but there are logistical challenges to the preparation of an intervertebral disc space via an axial access channel. The process of addressing these challenges impacts certain aspects of the tools intended for use in this manner.

Trans-Sacral Axial Access.

The trans-sacral axial access method illustrated in FIG. 2, eliminates the need for muscular dissection and other invasive steps associated with traditional spinal surgery while allowing for the design and deployment of new and improved instruments and therapeutic interventions, including stabilization, motion preservation, and fixation devices/fusion systems across a progression-of-treatment in intervention.

Figure 1:
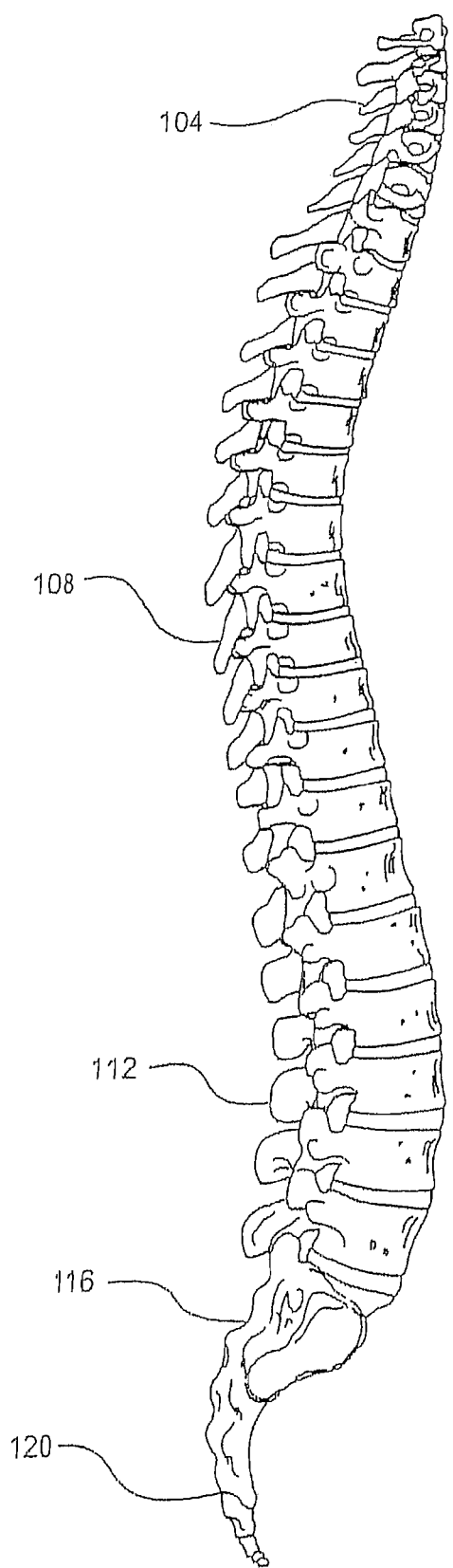
FIG. 1 identifies the sections of a human spine.
Figures 2A, 2B, 2C:
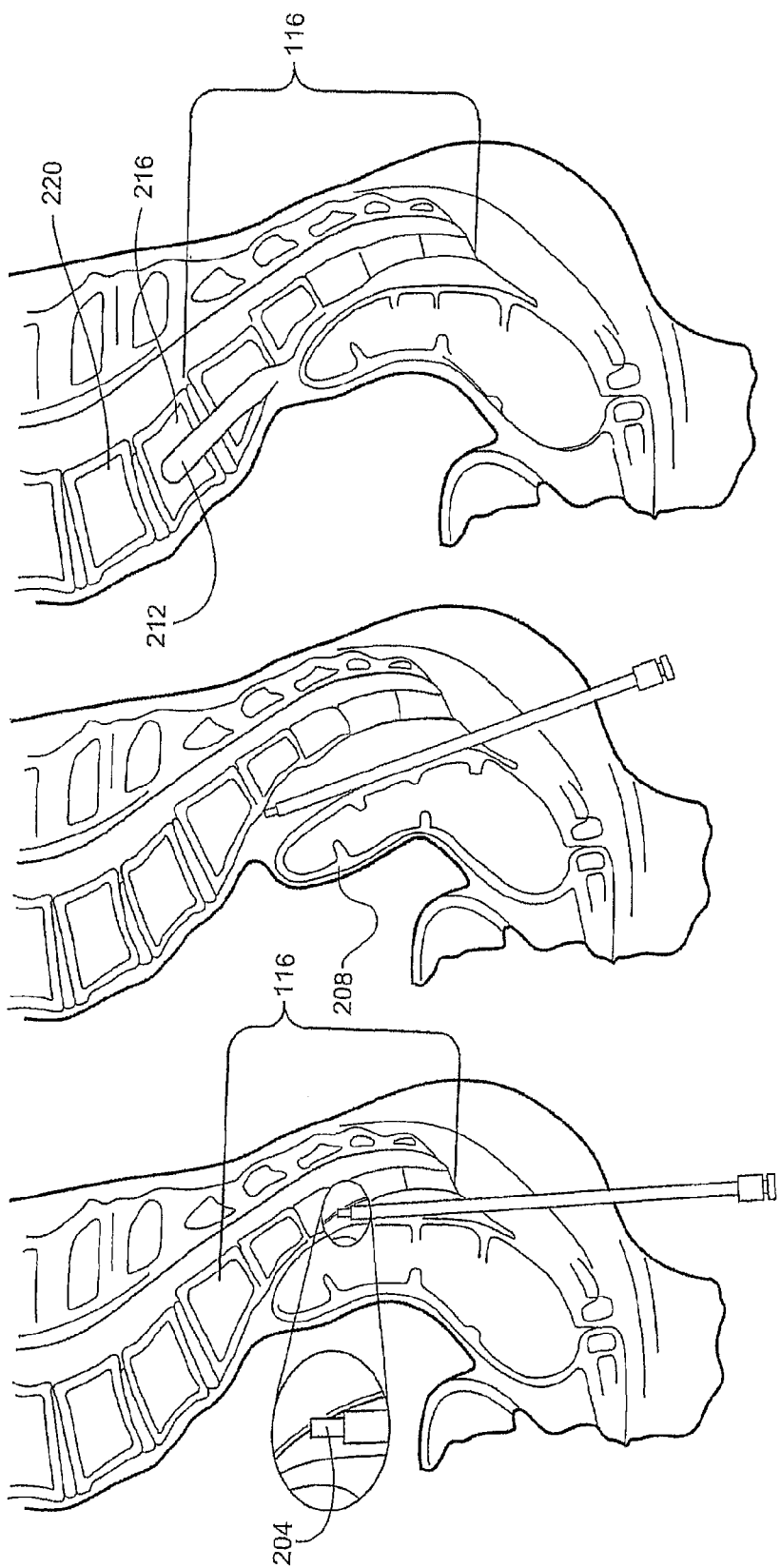
FIGS. 2A-2C illustrate an anterior trans-sacral axial access method of creating an axial channel in the spine which can be used to prepare an axial channel in the spine for use with the present disclosure.

FIGS. 2A-2C provide an introductory overview of the process with FIGS. 2A and 2B showing the process of "walking" a blunt tip stylet 204 up the anterior face of the sacrum 116 to the desired position on the sacrum 116 while monitored using one or more fluoroscopes (not shown). This process moves the rectum 208 out of the way so that a straight path is established for the subsequent steps. FIG. 2C illustrates a representative trans-sacral axial channel 212 established through the sacrum 116, the L5/sacrum intervertebral space, and into the L5 vertebra 216. If therapy is being provided to the L4/L5 motion segment then the trans-sacral axial channel 212 would continue through the L5 vertebra 216 and into the L4/L5 intervertebral space. In certain types of therapy provided to the L4/L5 intervertebral space the trans-sacral axial channel 212 would continue through the L4/L5 intervertebral space and into the L4 vertebra 220.

The discussion of FIG. 2 provides context for the present disclosure. Previous applications (some now issued as United States patents) with common assignee have included a description of an alternative access method that is a posterior trans-sacral axial spinal approach rather than an anterior trans-sacral axial spinal approach. (See e.g., U.S. Pat. No. 6,558,386 for Axial Spinal Implant and Method and Apparatus for Implanting an Axial Spinal Implant Within the Vertebrae of the Spine as this patent describes the anterior trans-sacral axial approach illustrated in FIG. 2 and U.S. Pat. No. 7,530,993 for Method of Spinal Fixation which describes the access method and tools—both patents are incorporated by reference in their entirety.)

Preparation with Cutters.

Figure 3:
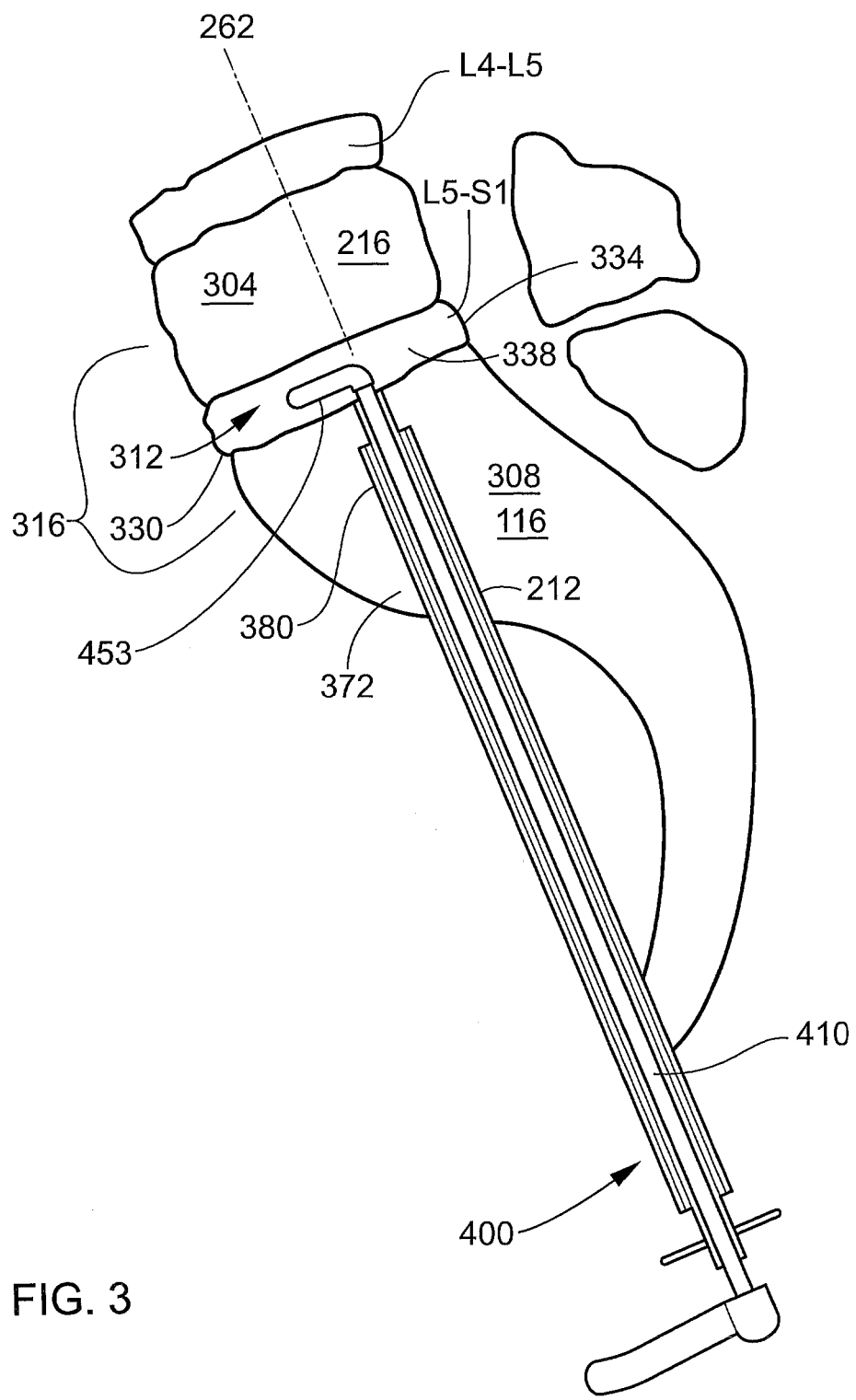
FIG. 3 shows a cutter assembly inserted into an axial channel with the cutter blade in an extended position.

Referring to FIG. 3, a cutter 400 is inserted through the axially aligned anterior tract 372 defined by the lumen of the dilator sheath 380 and the axial channel 212 which is difficult to see as the dilator sheath 380 substantially fills the axial channel 212 as it passes through the sacrum 116. (One of skill in the art will appreciate that the axial channel 212 may be extended axially by a sequence of steps so that the length of an axial channel in one figure may be different from another figure such that the axial tract may include additional vertebral bodies or intervertebral disc spaces). One of skill in the art will appreciate that due to anatomical differences the axial channel for some therapies may not cross the sacrum and may enter through another portion of the spine.

As shown in FIG. 3, motion segment 316 includes the proximal vertebra 308 (the sacrum 116), the intervertebral space 312 (in this case the L5-S1 space with disc 330, annulus fibrosus 334 and nucleus 338), the distal vertebra 304 (in this case L5 216). The cutter 400 comprises a cutting blade (e.g., cutter blade 453 which refers collectively to any blade configuration) which is remotely manipulable. The manipulations of the cutter blade 453 may include retracting the cutter blade 453 into the cutter assembly 400 so that the maximum radius of the cutter assembly 400 is reduced and the cutter assembly with the cutter blade 453 in a retracted position may be advanced through the axial channel 212. After reaching the location where the cutter blade 453 is to be operated, the cutter blade 453 may be extended.

As shown in FIG. 3, the centerline 262 of the cutter assembly 400 is very close to the centerline of the axial channel 212 due to the fit of the dilator sheath 380 in the axial channel 212 and the fit of the cutter assembly 400 within the dilator sheath 380. When the cutter blade 453 is extended as shown in FIG. 3 the cutter blade 453 may be substantially transverse to the centerline 262 of the cutter 400. The cutter blade 453 in the extended position is thus extended substantially laterally into the nucleus 338 of the spinal disc 330.

The cutter shaft 410, cutter sheath 430 (shown in FIG. 4) and the handle components are preferably co-configured to enable the cutter blade 453 and the cutter shaft 410 to which it is attached be able to be "pushed-pulled" so as to retract the cutter blade 453 into the cutter sheath and then extend the cutter blade 453 from the distal end of the cutter sheath as needed. More specifically, the cutter blade edges(s) of the cutter blade 453 are retracted into the cutter sheath 430 (FIG. 4) for delivery into the intervertebral disc space 312. Once the cutter assembly 400 is in position, the cutter blade 453 is extended distally and rotated using the handle to cut tissue within the intervertebral disc space 312. Whenever the surgeon has a need to withdraw the cutter blade 453 from the surgical site, the cutter blade 453 is again retracted into the cutter sheath 430 (FIG. 4) for removal of the cutter assembly unit 400 from the axial channel 212.

The cutter assembly 400, cutter blade 453 and cutter assembly shaft 410 are shown schematically in FIGS. 4A-4B and not necessarily to scale to one another or to the axial channel 212.

Cutters can be used to perform nucleectomies via insertion into a disc space to excise, fragment and otherwise loosen nucleus pulposus and cartilage from endplates from within the disc cavity and from inferior and superior bone endplate surfaces. As noted within this disclosure, removal of cartilage in a manner which results in controlled bleeding within the intervertebral disc space 312 will promote bone growth, which is believed to be desirable in an arthrodesis procedure.

With reference to the exemplary embodiments of FIGS. 4A-4B, the cutter assembly 400 (also referred to as simply a cutter) includes: a cutter shaft 410 with a distal end 412 and a proximal end 414; a cutter blade 453 connected to the distal end 412 of the cutter shaft 410; a handle 416 connected to the proximal end 414 of the cutter shaft by an attachment process such as a set screw or pin; a cutter sheath 430 placed concentrically over the shaft 410; and a shaft sleeve 418 (shown in subsequent drawings).

Figure 5A:
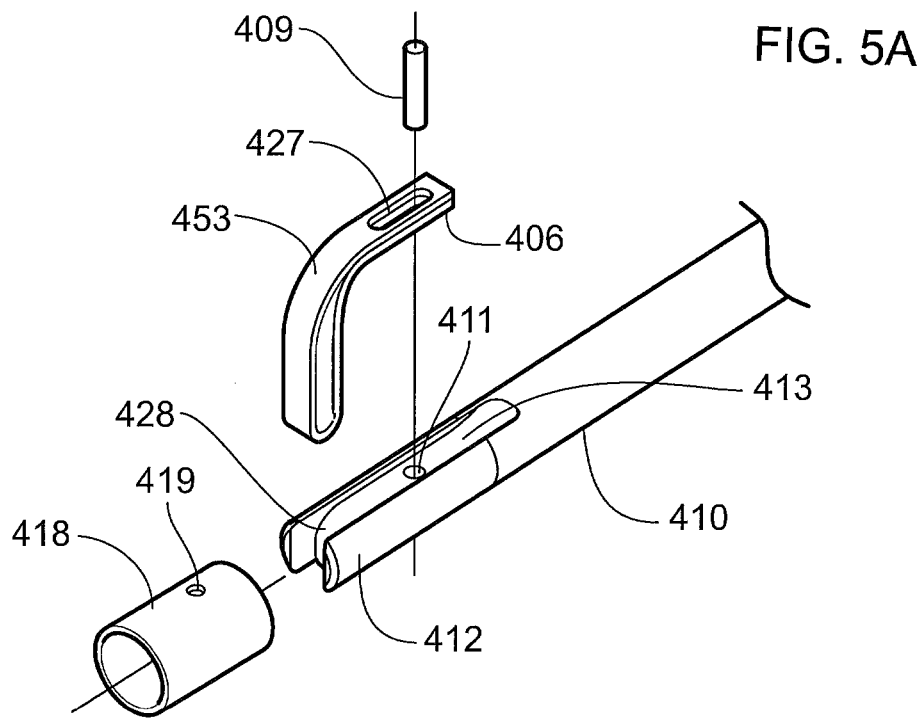
FIGS. 5A-5B show one method for connecting a cutter blade to a cutter shaft.
Figure 5B:
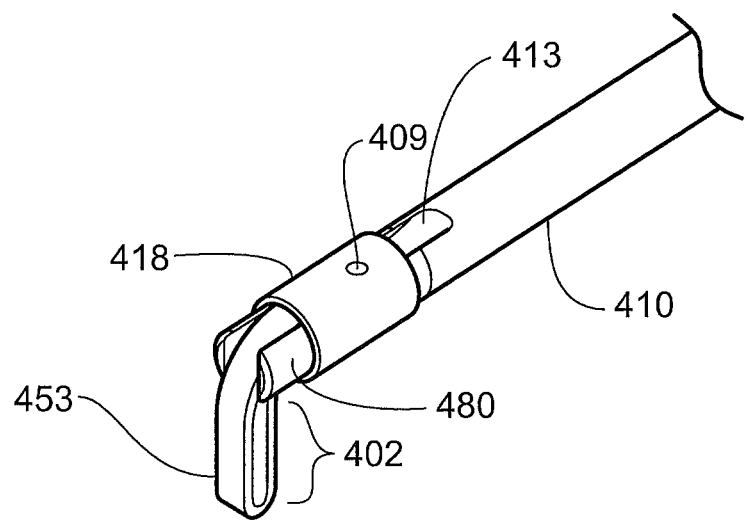

FIGS. 5A-5B illustrate one method of connecting a cutter blade 453 to a cutter shaft 410. Before the pin 409 is inserted, the longitudinal portion 406 of the cutter blade 453 is placed into a slot 413 near the distal end 412 of the cutter shaft 410. The cutter blade slot 427 may be aligned with the cutter shaft hole 411 within the shaft slot 413. A pin 409 may be placed through a shaft sleeve hole 419 in a shaft sleeve 418, through a cutter blade slot 427 (visible in FIG. 5A), and a cutter blade hole 407 on the opposite side of the longitudinal portion 406 of the cutter blade 453 (best seen in FIG. 10A). The pin passes through cutter blade hole 407 and into a cutter shaft hole 411 in a cutter shaft slot 413.

The shaft slot 413 is dimensioned to accommodate a cutter blade 453. The width of the shaft slot 413 is approximately the same as the width of the longitudinal portion 406 of the cutter blade 453. The curvature 428 at the distal end of the shaft slot 413 accommodates the curvature of the cutter blade 453 between the longitudinal portion 406 and the portion of the cutter blade that may be extended 402 (also known as the cutter blade arm 402) (which defines the reach or throw of the cutter blade 453). The shaft slot 413 provides torsional support to the cutter blade arm 402 while the curvature 428 at the distal end of the slot 413 provides axial support to the cutter blade arm 402 to work in conjunction with cutter blade edge geometries to reinforce the cutter blade 453. The optional cutter shaft extension 480 provides additional support to the cutter blade 453 to reduce the tendency of the cutter blade 453 to flex when rotated against resistance from tissue.

The shaft sleeve 418 when pinned, effectively serves to align and fix the shaft 410 and the longitudinal portion 406 of the cutter blade 453. For purposes of illustration, the pin 409 that fixes the cutter blade 453 to the shaft 410 may be approximately 0.06 inches (1.5 mm) in diameter.

As cutter blade hole 407 (as seen in FIG. 8A) is pinned to the cutter blade shaft 410, the cutter blade 453 is affixed to the cutter blade shaft 410. The cutter blade slot 427 allows some relative motion of the slotted portion of the longitudinal portion 406 relative to the pinned portion of the longitudinal portion 406 to accommodate the change of shape of the cutter blade 453 as it goes from sheathed to extended and back to sheathed.

The rest of the cutter assembly 400 components can be fixedly secured to each other using any known suitable fixation mechanisms.

FIGS. 6A-6D provide a series of views of a cutter assembly 400. FIG. 6A is a top view of the cutter assembly 400. FIG. 6B is a rear view of the cutter assembly 400. FIG. 6C is a cross section of FIG. 6B. FIG. 6D is an enlarged portion of FIG. 6C.

As shown in FIGS. 6A and 6D, the shaft slot 413 (FIG. 5A) in the cutter shaft 410 may be oriented so that the handle 416 is aligned with the blade arm 402 (when extended). While not required, this relationship between the handle and blade is a useful way to allow the surgeon to keep track of the position of the extended blade arm 402 by knowing rotational position of the handle 416.

As best seen in FIG. 6D, the travel range 440 of the cutter sheath 430 is limited at the proximal end by a proximal end stop 444 attached to the cutter shaft 410. The travel range 440 of the cutter sheath 430 is limited at the distal end by a shoulder 448 on the cutter shaft 410.

One of skill in the art will appreciate that while the cutter blades 453 are to be used with a single patient and then disposed, that, certain components such as the handle 416, cutter shaft 410, and cutter sheath 430 may be reusable. The handle 416 and cutter shaft 410 could be made as one integral component.

A sleeve or internal sheath liner (not shown) may be inserted inside the cutter sheath 430 to reduce friction. The cutter blade 453 may be formed from a shape memory alloy including a nickel-titanium shape memory alloy such as Nitinol™. The cutter sheath 430 may be made from an appropriate grade of stainless steel. To reduce the friction between the cutter blade 453 and the inner surface of the cutter sheath 430, a dry lubrication such as poly-tetrafluoroethylene (PTFE) may be used. Alternatively, the cutter sheath 430 or internal sheath liner may be made of a material with a coefficient of friction that is lower than that of the cutter blade. If this component is to be reused, it may be chosen for its ability to withstand multiple sterilization cycles. Ultra-high molecular weight polyethylene (UHMWPE) is one such material.

Use of a Sequence of Tools.

Figure 7:
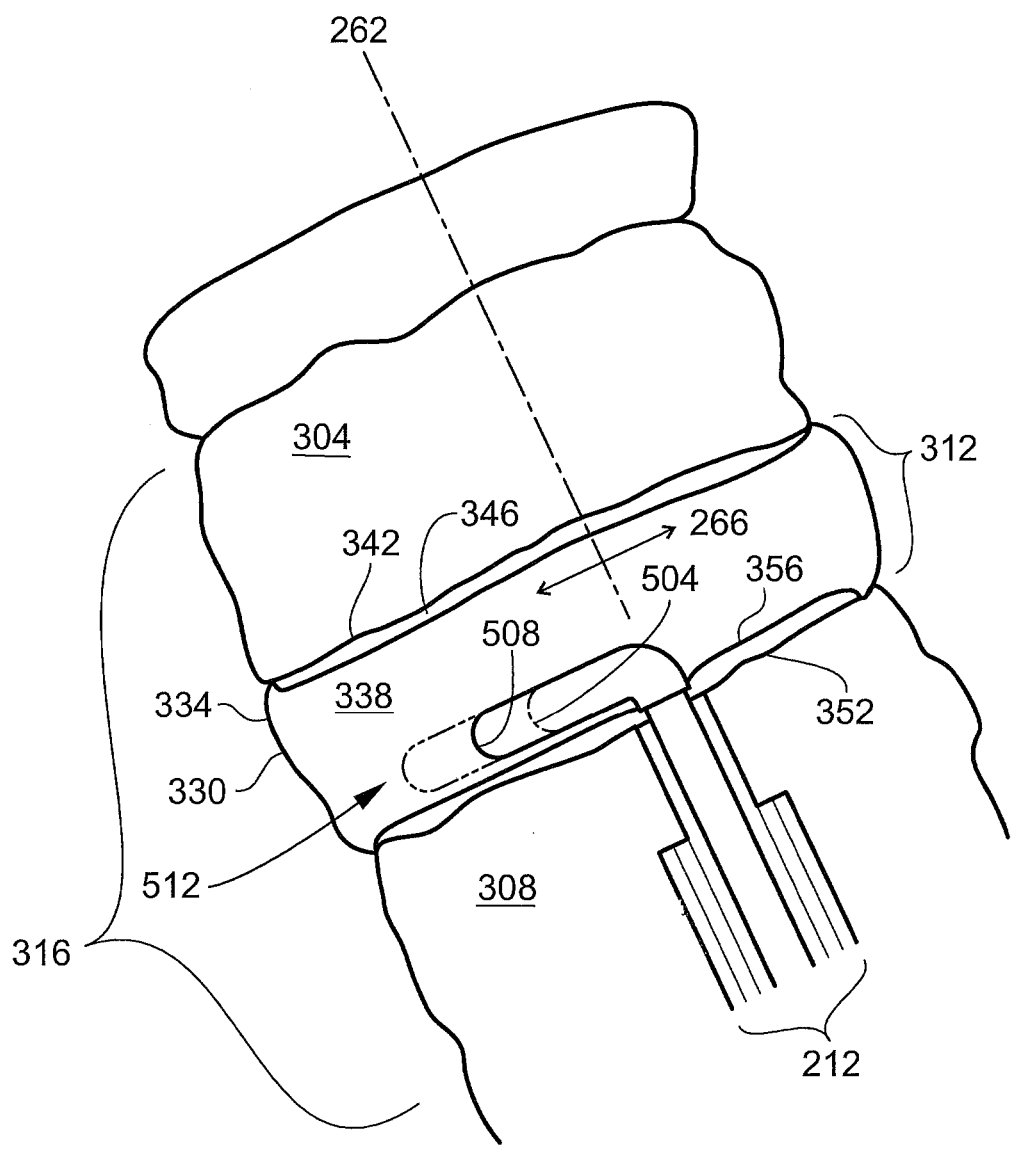
FIG. 7 addresses the concept of a series of cutter blades of different throw lengths within an intervertebral disc space.

After this introduction to cutters and cutter components, it is useful to discuss why a sequence of cutters may be used while preparing the interior of an intervertebral disc space 312. FIG. 7 shows a first example. In FIG. 7 a motion segment 316 including a distal vertebral body 304, an intervertebral disc space 312 (with an intervertebral disc 330 including an annulus fibrosus 334, and nucleus pulposus 338 and bounded by the endplates), and a proximal vertebral body 308 are shown. For purposes of this example, it is not important which vertebral bodies are involved beyond the need for them to be adjacent vertebral bodies.

FIG. 7 includes the endplate 342 of the distal vertebral body 304 and a representation of the layer of cartilage 346 located on the endplate 342 which defines one portion of the intervertebral disc space 312. Assuming the route of access is a trans-sacral axial access, from the point of reference of the intervertebral disc space 312, endplate 342 would be the superior endplate. Likewise FIG. 7 includes the endplate 352 of the proximal vertebral body 308 and a representation of the layer of cartilage 356 located on the endplate 352 which defines one portion of the intervertebral disc space 312. Assuming the route of access is a trans-sacral axial access, from the point of reference of the intervertebral disc space 312, endplate 352 would be the inferior endplate. Each endplate has a superior surface and an inferior surface.

One of skill in the art will recognize that the inclusion of the cartilage layers 346 and 356 is for purposes of discussing the use of cutters and other tools and is not intended to be an anatomically correct and appropriately dimensioned representation of cartilage.

The position of the cutter within the intervertebral disc space may be visible to the surgeon under real-time fluoroscopic imaging (possibly both anterior/posterior and lateral imaging).

In order to illustrate a concept, FIG. 7 includes representations of three different cutter blades 504, 508, and 512 of differing throw lengths. One of ordinary skill in the art will appreciate that one method for cutting the nucleus 338 would use a series of cutter blades (504, 508, 512, and possibly another longer blade) to gradually cut the nucleus 338. One of ordinary skill in the art will understand that these three blades of different throw lengths (sometime called reaches) would be used sequentially from shorter to longer and it is only for the point of illustration that three different blade lengths are shown simultaneously in FIG. 7. To provide context, the reach of a series of cutter blades used in a particular procedure may range from between 6 mm and 12 mm and often about 10 mm for a small cutter blade and between 15 mm and 30 mm often 18 mm for a large cutter blade. One of skill in the art will recognize that these ranges are illustrative and could be different. It will be understood that the optimum throw for cutter blades depends on several factors, including patient anatomy and (axial) entrance point into the disc space, as well as issues related to sagittal symmetry of the spinal disc. Moreover, for safety reasons, it may be desirable to limit the length of the cutter blade to preclude a throw that is too close to the disc edge, in other words to avoid making contact between the cutter blade and the annulus fibrosus to preclude compromising the annulus fibrosus.

Note that the cutter blades 504, 508, and 512 when extended are transverse to the centerline of the cutter shaft 262 and parallel to the axis 266 that is perpendicular to cutter blade centerline 262. The cutter blades are also close to parallel to the distal endplate 342 and proximal endplate 352 and the layers of cartilage 346 on the endplate of distal vertebral body 304 and cartilage 356 on the endplate of the proximal vertebral body 308, respectively.

In this example, the successively longer cutter blades 504, 508, and 512, could be rotated 360 degrees or more around the centerline 262. Some surgeons may prefer to work on one segment at a time by rotating the cutter handle a fraction of 360 degrees (perhaps approximately 90 degrees) then rotating the cutter handle in the opposite direction to return to the position occupied by the cutter. Thus, the process tends to proceed while working on radial quadrants. Sometimes this short movement is compared to the movement of windshield wipers on an automobile.

In addition to using a series of cutter blades with sequentially increasing throws, the surgeon will need to adjust the axial position of the cutter blade by sliding the cutter forward (in the direction towards distal) relative to the motion segment so that the cutter blade moves sequentially closer to the cartilage 346 on the endplate 342 on the distal vertebral body 304. The surgeon may opt to create a first space relatively close to the proximal vertebral body by using a sequence of cutters of increasing throws then repeating the process with the cutter extended further into the nucleus (and repeating the sequence of blades of increasing throws).

Alternatively, the surgeon may choose to use one or more cutters with a first throw to create a space approximating a cylinder that is substantially the height of the space between the two layers of cartilage and a radius approximately equal to a first blade throw. This process may involve the use of a radial cutter blade with a given throw length followed by one or more cutter blades at a different blade angle(s) (for example 45 degrees) but the same throw length. Once the cutting is complete for a given throw length, the surgeon moves to cutter blades of a longer throw length starting again with a radial cutter blade. This process may be repeated with cutter blades of increasing blade throws until the desired amount of space is created.

The nature of the therapeutic procedure and the patient anatomy will determine the maximum cutter blade throw length required. Certain procedures may tend to use a greater number of cutter blade throw lengths to make smaller incremental increases in throw length. Other procedures may simply use a small throw length then move to the maximum throw length needed to prepare the intervertebral disc space.

As the nucleus material is cut, the surgeon may periodically remove the cutter from the axial channel and use any appropriate tissue extractor tool. U.S. Pat. No. 7,500,977 (referenced above) describes several retractable tissue extractors that may be used for this purpose.

U.S. Pat. No. 7,500,977 (referenced above) noted that when preparing an intervertebral disc space for a fusion procedure, it can be advantageous to use cutters to scrape away the cartilaginous endplate and roughen the vascularized tissue layer in the vertebral body so as to cause bleeding, which is desirable in order to facilitate bone growth and to promote fusion of the vertebral bodies of the relevant motion segment.

Use of Cutters to Prepare Endplates.

FIG. 8 shows a series of views of a closed loop cutter blade 500 that is adapted to scrape away the cartilaginous endplate and roughen the vascularized vertebral body endplates so as to cause bleeding. Visible are the cutter blade hole 407 and the cutter blade slot 427. The cutter blade arm 402 is joined to the longitudinal portions 406 by a pair of transitional sections 470. While the precise position is not particularly relevant, in the area where the two transitional sections 470 meet the two longitudinal sections 406, the two ends of the cutter blade meet. This point of contact could be deemed the place where the loop is closed. However, it may be simpler to call the loop closed at 550 which is placed at cutter blade hole 407 and the currently adjacent portion of cutter blade slot 427 as those two are joined when the cutter blade is attached to the cutter assembly at the blade shaft (see FIG. 5).

Cutter blade 500 can be said to have six different cutting edges 504, 508, 512, 516, 520, 524. Three cutting edges 504, 508, 512 on one side and three cutting edges 516, 520, 524 on the other side. Edges 504 and 516 are on the proximal portion 536 of the blade arm 402 of the cutter blade 500, that is the portion of the blade arm that is closer to the handle 416 (FIG. 4A) than the other portion of the closed loop that is the distal portion 542 of the blade arm 402.

When inserted into the intervertebral disc space, the exterior of the proximal portion 536 will generally face the endplate on the proximal vertebral body (whether or not the proximal portion is parallel to the endplate). Edges 508 and 520 are on the distal portion 542 of the blade arm 402. When inserted into the intervertebral disc space, the exterior of the distal portion 542 will generally face the endplate on the distal vertebral body (whether or not the distal portion 542 is parallel to the endplate). Edges 512 and 524 are on the tip 548 of the cutter blade 500 between the distal portion 542 and the proximal portion 536 of the blade arm 402 and connecting the distal arm 560 and the proximal arm 564.

The cutting edges along the proximal portion 536 and the distal portion 542 of the blade arm 402 do not extend over the entire blade arm 402. As indicated in FIG. 7, it is contemplated that a series of cutter blades of increasing length will be used so that the cutter blade edges do not need to extend over the entire range that was previously cut by a previous cutter blade.

Note that the sides of a cutter blade are not necessarily flat. The sides (sometimes called faces) have features that are visible when looking at that side or face of the object (just as the indentations on one of the six faces of a single die from a pair of dice are visible when looking at that face or side of the die).

In each case, the six cutting edges are on the outer perimeter 556 of the closed loop rather than on the inside perimeter 552 as the outer perimeter 556 is the better choice for edge placement in order to contact the cartilage on an endplate. By placing the cutting edges on the outer perimeter 556 of the closed loop, the cutter blade 500 is adapted to maximize the effectiveness of the cutter blade in cutting either the cartilage 356 (FIG. 7) on the proximal endplate 352 (likely to be the inferior endplate when viewed in context of the intervertebral disc space 312) or the cartilage 346 (FIG. 7) on the distal endplate 342 (likely to be the superior endplate when viewed in the context of the intervertebral disc space 312).

By having cutting edges on both sides of cutter blade 500, the surgeon may cut nucleus material while rotating the cutter blade in the clockwise direction and also while rotating the cutter blade in the counter-clockwise direction. Clockwise and counterclockwise are dependent on orientation. One way of defining clockwise would be as viewed from the cutter assembly while looking from proximal towards distal end of the cutter assembly. This would match the way the surgeon would view rotation of the cutter handle.

While being bidirectional is a useful feature, not all cutter blades must have cutting edges on both sides. Some cutter blades may have one type of cutting edge on one side and a second type of cutter blade on the second side. While it may be advantageous for some cutter blades to have blade edges on the tips of the cutter blade, some cutter blades may not have a blade edge in the tip or may have a different blade edge type in the tip 548 than in the distal portion 542 and proximal portion 536.

The cutting blade 500 has a gap 528 within the closed loop that may allow material to pass through the gap while the cutter blade 500 is being rotated within the intervertebral disc space 312. This may add another aspect to the cutting action while reducing the resistance to the cutter blade 500 moving through the intervertebral disc space 312. Other cutter blades may have less of a gap between the distal and proximal portions or no gap at all.

A cutter blade without a gap large enough to allow material to pass through the gap in the inside perimeter of the closed loop receives benefit from the closed loop as noted above in that having the closed loop connected to the cutter shaft provides two points of connection for the cutter blade and provides at least one point of connection from each part of the cutter blade to the cutter shaft 410 in the event of a break in the cutter blade.

Thin Disc Cutter Blades.

Figure 9:
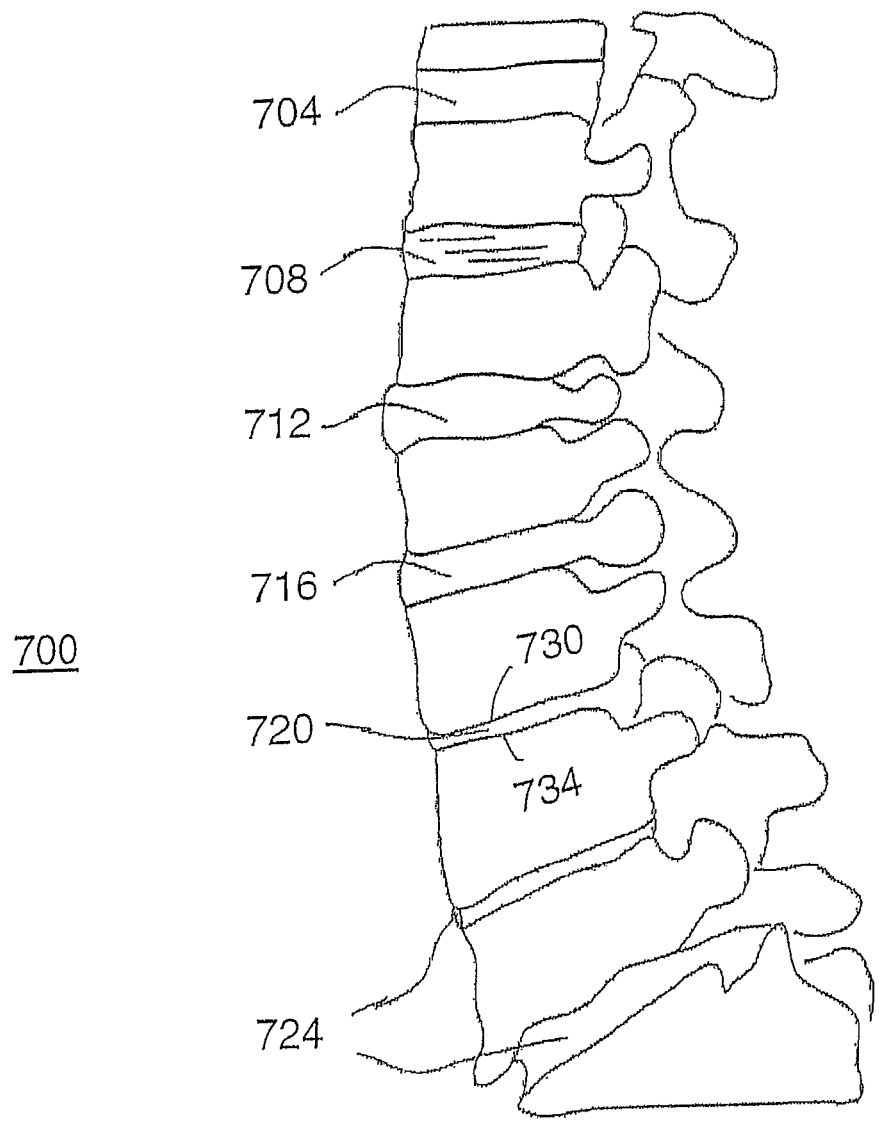
FIG. 9 shows a lateral view of a portion of a human spine.

FIG. 9 shows a lateral view of a portion of a human spine 700. Disc 704 illustrates a normal healthy disc. Disc 708 is a deteriorating disc. Disc 712 is a bulging disc. Disc 716 is a herniated disc. Disc 720 is a thinning disc and is noteworthy in that the space between endplates 730 and 734 is greatly reduced in comparison with the normal disc 704. Likewise discs 724 which are degenerated discs with osteophyte formations are also thin discs. Closed loop cutter blades such as cutter blade 453 in FIG. 3 and again in FIG. 5 may not be sufficiently thin to operate within a thin disc.

Figure 10:
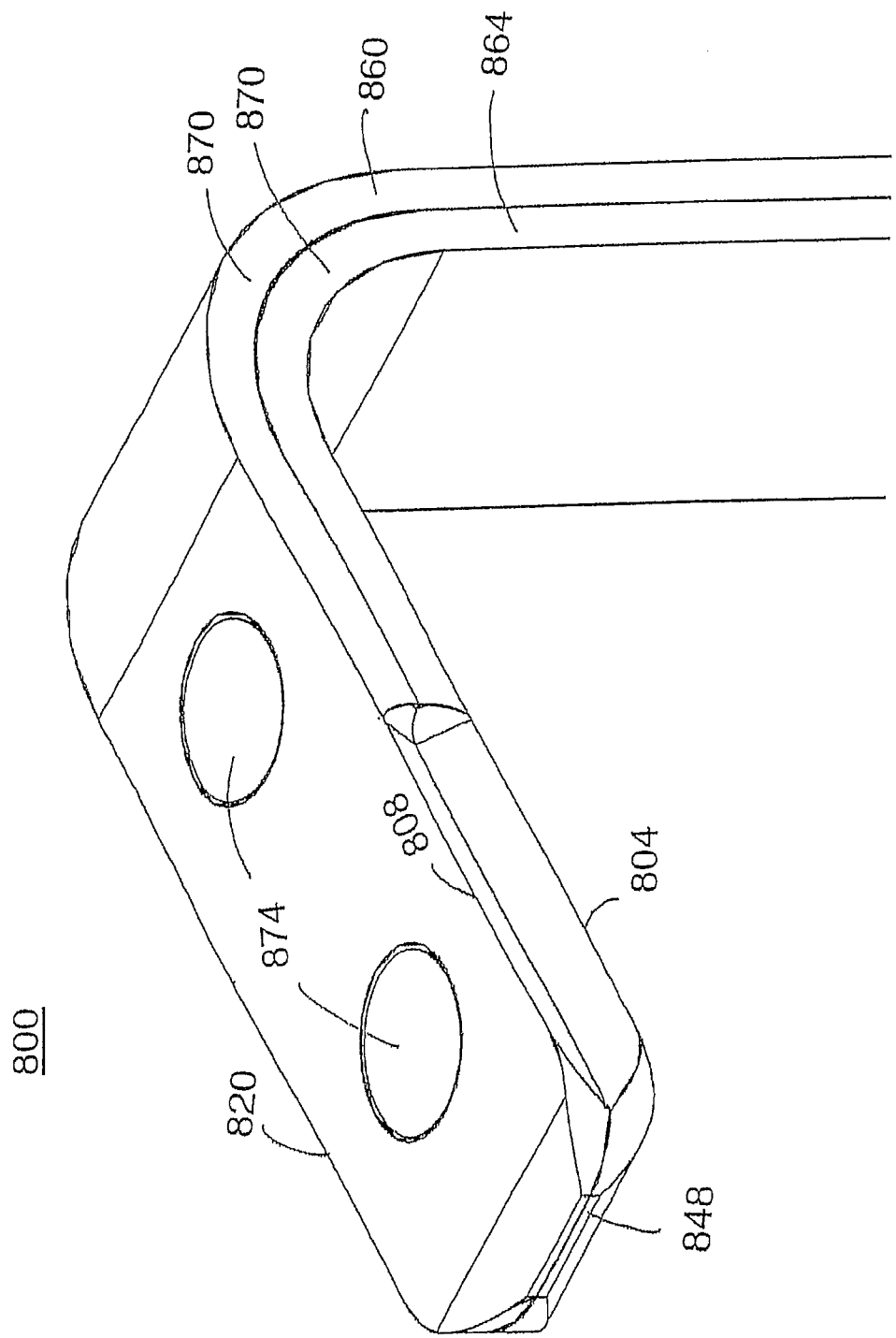
FIG. 10 shows a top perspective view of a thin cutter blade for use in situations such as a thin disc.

FIG. 10 shows a top perspective view of a thin cutter blade 800 for use in situations such as a thin disc. The thin cutter blade 800 has many features that are similar to the cutter blade 500 discussed in connection with FIG. 8. Thin cutter blade 800 has blade edges 808 and 820 on the distal arm 860 and blade edges 804 and 816 (not visible here) on the proximal arm 864.

Unlike the closed loop cutter blade 500, there is not a gap between the distal arm 860 and the proximal arm 864 in the vicinity of the blade edges. Thus the thickness of the cutter blade is on the order of magnitude of only 0.050 inches which is considerably less than found in the closed loop cutter blades such as cutter blade 500 in FIG. 8.

Two rivets 874 are added to retain the flush relationship between the distal arm 860 and the proximal arm 864. After the rivets 874 are pressed, the rivets 874 are made flush with the surface of the distal arm 860 and with the surface of the proximal arm 864 (lower side of rivets not visible in this view). The tip 848 does not have a cutting edge but is rounded or beveled.

Figure 11A:
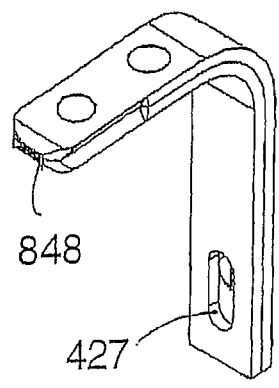
FIGS. 11A-11D provide additional views of the thin cutter blade of FIG. 10.
Figure 11D:
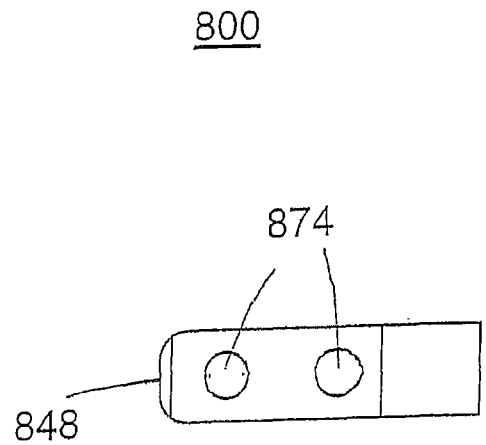
Figure 11B:
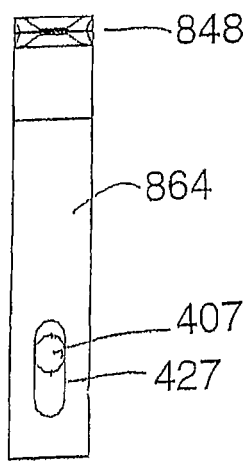
Figure 11C:
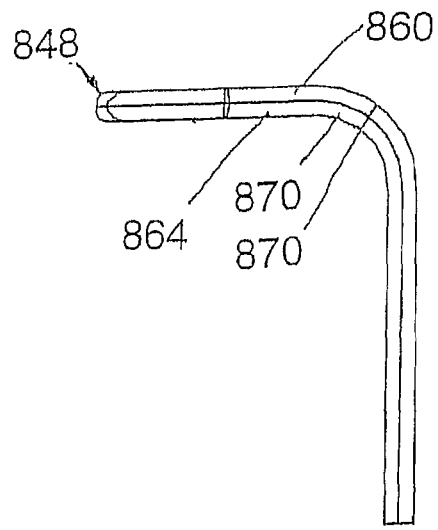

FIGS. 11A-12D provide additional views of thin cutter blade 800. FIG. 11A is a top perspective view of thin cutter blade 800 much like FIG. 10. As FIG. 11A shows the entire thin cutter blade 800 it includes cutter blade slot 427. FIG. 11B, a front view of thin cutter blade 800 shows cutter blade slot 427 that is on the proximal arm 864 and visible through the cutter blade slot 427 is the cutter blade hole 407 that is on distal arm 860. The use of a combination of a slot and a hole allows the proximal arm 864 to move relative to the distal arm 860 as the thin cutter blade 800 is encircled by the cutter sheath and thus constrained to move away from the shape shown in FIG. 11. As the thin cutter blade 800 changes shape, the curvatures in transitional sections 870 change. FIG. 11C is a side view of thin cutter blade 800 and FIG. 11D is a top view of the thin cutter blade 800.

Blade Angles.

Figure 12:
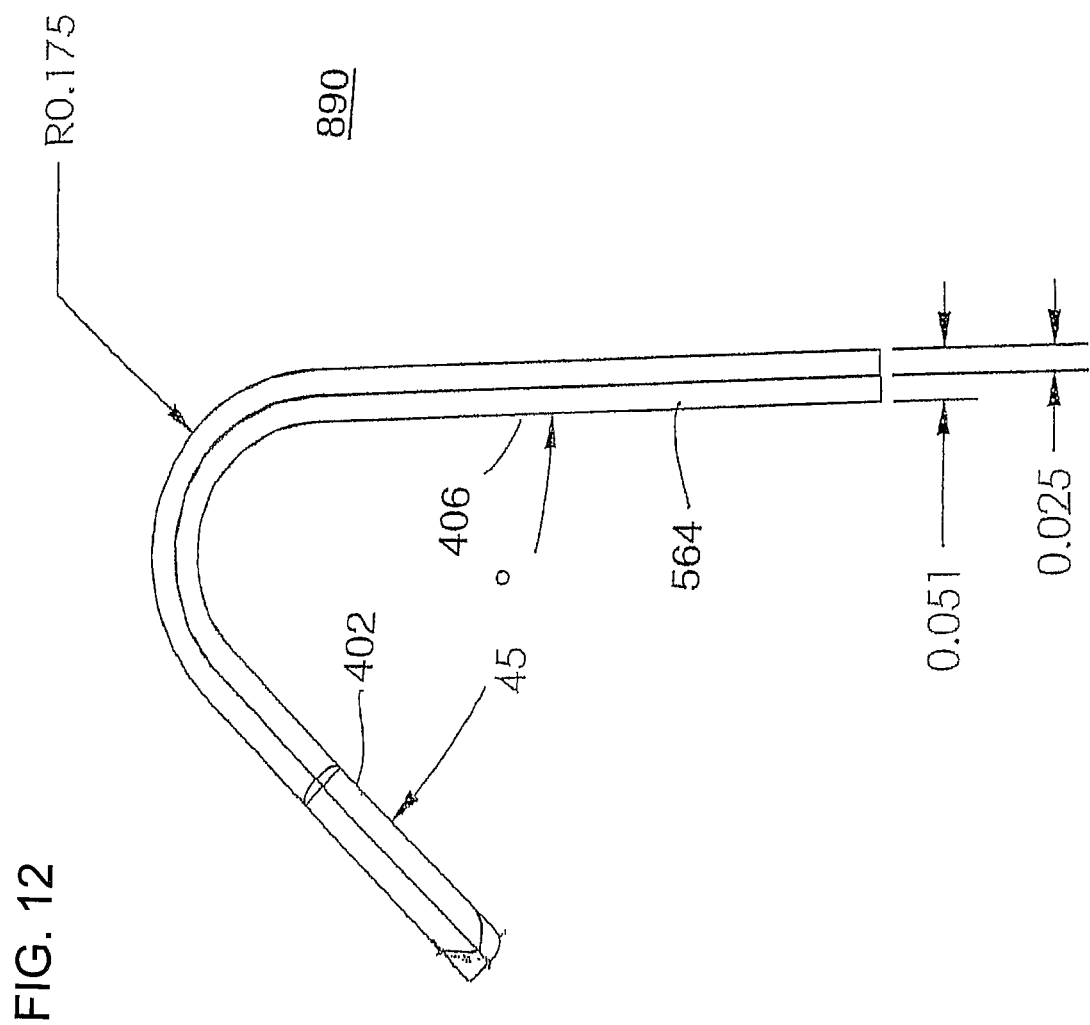
FIG. 12 provides a side view of a thin cutter blade that has a 45 degree angle between the blade arm portion of the proximal arm and the longitudinal portion of the proximal arm.

FIG. 12 provides a side view of a thin cutter blade 890 that has a nominal 45 degree angle between the blade arm 402 portion of the proximal arm 564 and the longitudinal portion 406 of the proximal arm 564. Thin cutter blades with a range of angles may be useful for working in thin discs at the endplates that partially define the intervertebral disc space (see endplates 342 and 352 in FIG. 7) where the endplates are not substantially perpendicular with the centerline 262 of the cutter assembly 400 as is the case in FIG. 7. The angles may range from between about 25 to about 155 degrees but there may be more demand for angles in the range of between about 40 to about 140 degrees. One of skill in the art will recognize that tools may be provided with a series of nominal blade angles and that a nominal 45 degree blade angle may actually be slightly more or slightly less than 45 degrees and the precise blade angle may differ depending on how one chooses to make the measurement.

One of skill in the art will appreciate that if an endplate is arranged at an oblique angle with respect to an access channel, then one portion of the endplate will be "uphill" from the access channel and one section of the endplate will be "downhill" from the access channel with intermediate portions of the endplate transitioning from uphill to downhill. One can appreciate that a surgeon may wish to use a relatively neutral nominal 90 degree blade angle for at least some portions of the endplate as it transitions from uphill to downhill, a blade angle of less than about 90 degrees for the more pronounced downhill section, and a blade angle of more than about 90 degrees for the more pronounced uphill section.

One of skill in the art will recognize that to the extent that the cutter blades are produced in a finite number of nominal cutter blade angles, the actual measurement of the precise angle may deviate a few degrees (perhaps 5) from the nominal angle value. The actual angle may deviate over cycles of moving from the sheathed to the extended position.

In many situations a set of cutter blades of various combinations of throw lengths and angles (such as 45 degree, 90 degree, and 135 degree) may be sufficient. Some surgeons may feel that they obtain adequate results for some therapies with using just 90 degree and 45 degree cutter blades. Other angles could be used, including angles that deviate less from 90 degrees such as 60 degrees and 120 degrees, or angles that deviate more from 90 degrees such as 25 degrees and 155 degrees. Angles even closer to 90 degrees may be useful in some applications such as an angle in the vicinity of 105 degrees. Kits could include more than three angle values for the cutter blades. For example, a kit might include blades at 25, 45, 60, 90, 105, 120, 135 and 155 degree angles. With this range of blade angles, there is a wide variation of the extent to which the extended blades are transverse to the long axis of the cutter assembly, but in all these cases the cutter blades are significantly transverse to the long axis of the cutter assembly and to the longitudinal portions of the cutter blades.

Some surgeons may work by initially using a short 90 degree cutter blade, then using progressively longer 90 degree cutter blades (one or more longer cutter blades) to cut as much material within the intervertebral disc space 312 as can be safely handled using 90 degree cutter blades. Next, the surgeon may want to work with a short 45 degree cutter blade. Next the surgeon may want to work with one or more longer 45 degree cutter blades to remove material that would be difficult to access using a 90 degree cutter blade. Finally, in some cases, the surgeon may opt to use a short 135 degree cutter blade followed by one or more longer 135 degree cutter blades to cut nucleus material that is difficult to access using either a 90 degree or a 45 degree cutter blade.

Abrading Tools.

While vertebral endplates may be prepared for fusion with cutters as described above that access the endplates through a trans-sacral approach, an alternative tool that works more through abrasion rather than cutting may be useful in some situations. An abrading tool may allow for effectively and efficiently removing material from an endplate in a uniform manner.

Upcutter Abrading Tool.

Figure 13:
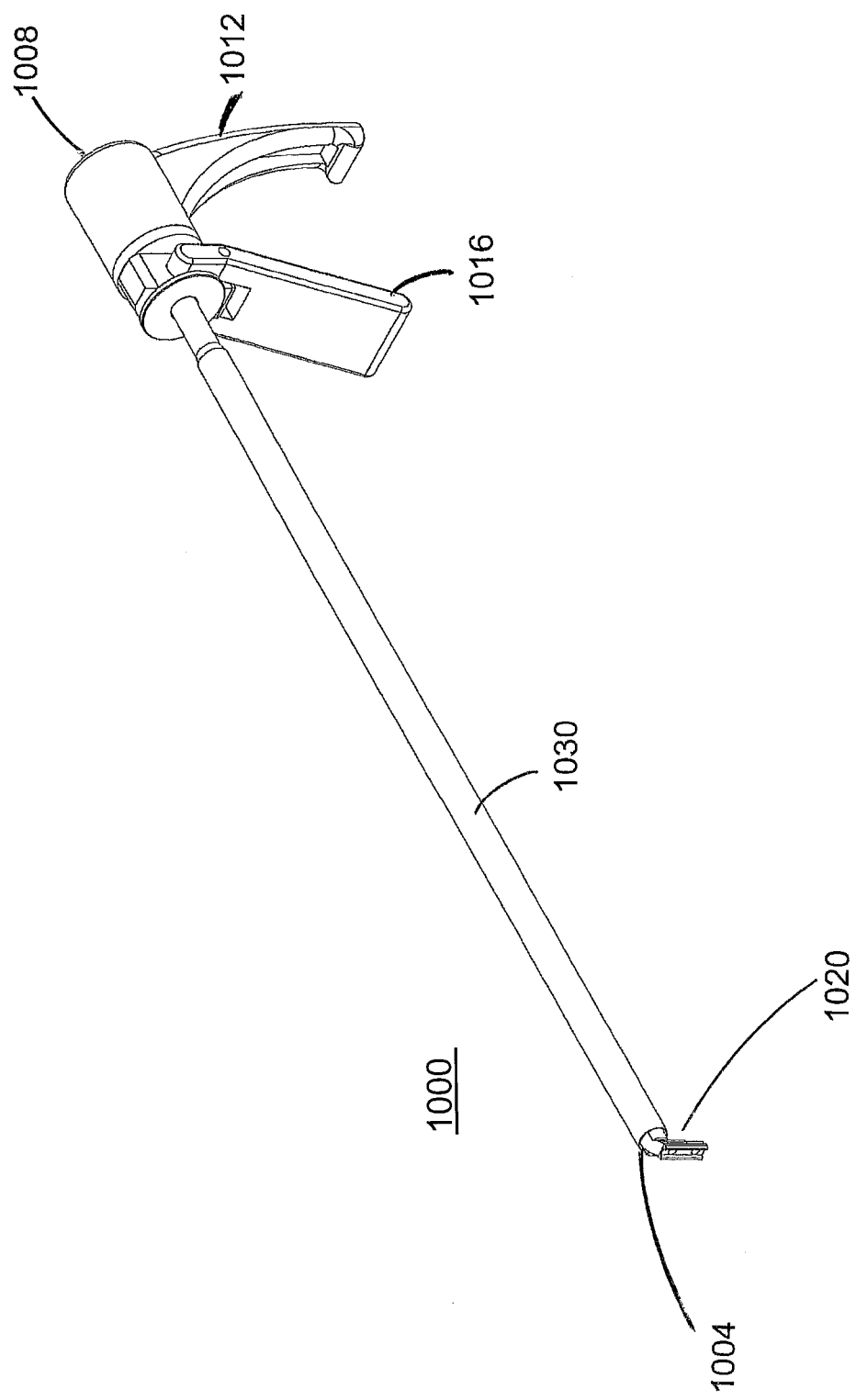
FIG. 13 provides a top perspective view of an upcutter abrading tool 1000.

FIG. 13 provides a top perspective view of an upcutter abrading tool 1000. The upcutter abrading tool 1000 has a distal end 1004 with an abrading blade 1020 intended for insertion via the access channel 212 (FIG. 7) to abrade the cartilage 346 on the distal vertebral endplate 342 of the distal vertebral body 304.

Upcutter abrading tool 1000 has a proximal end 1008 including a handle 1012 and a trigger 1016. Shaft sheath 1030 is between the distal end 1004 and the proximal end 1008.

Figure 14:
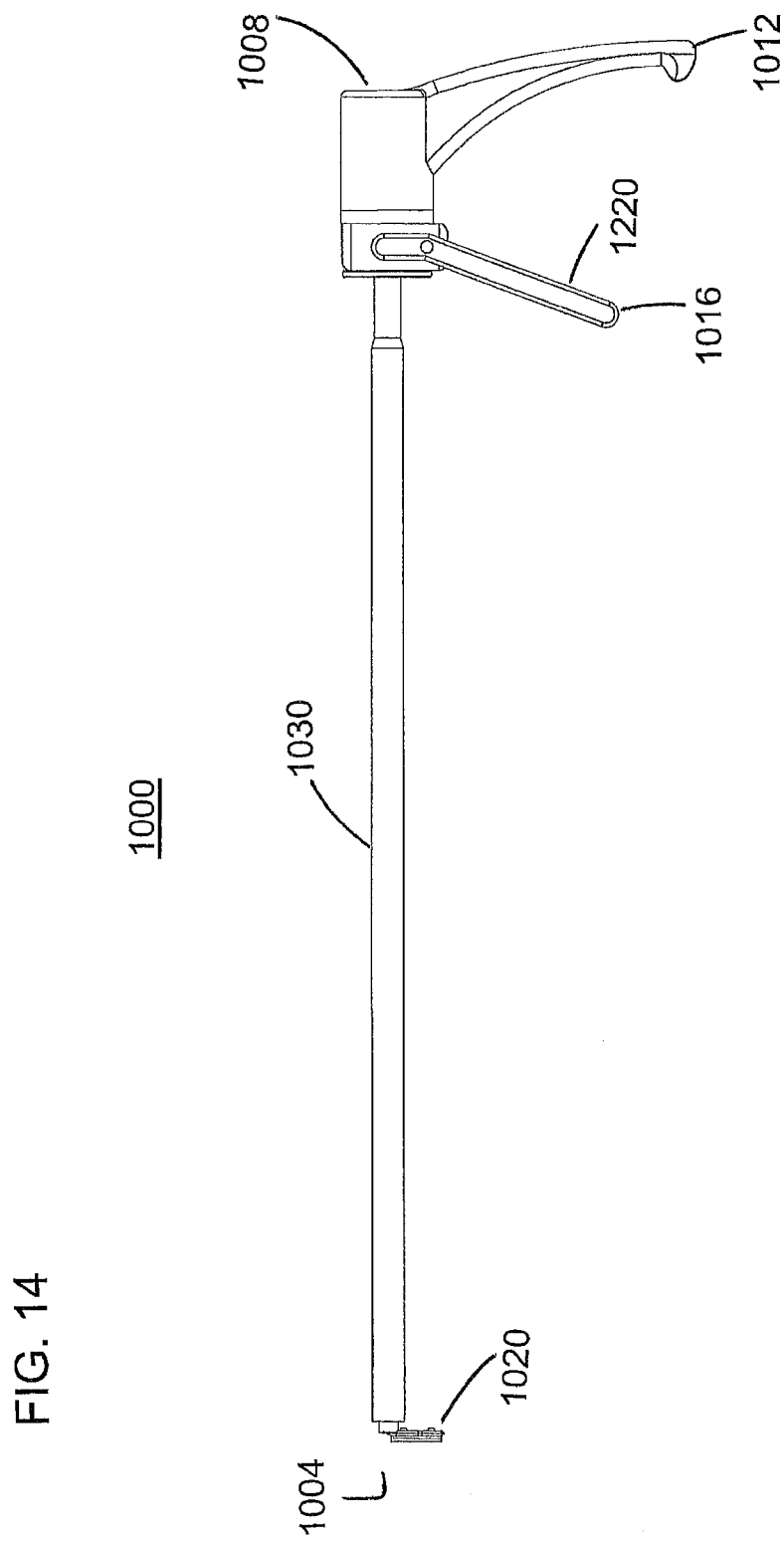
FIG. 14 provides a side view of the upcutter abrading tool 1000 of FIG. 13.

FIG. 14 provides a side view of the upcutter abrading tool 1000 of FIG. 13. Visible in this drawing are the various elements discussed in connection with FIG. 13.

Details on Abrading Blade.

Figure 15:
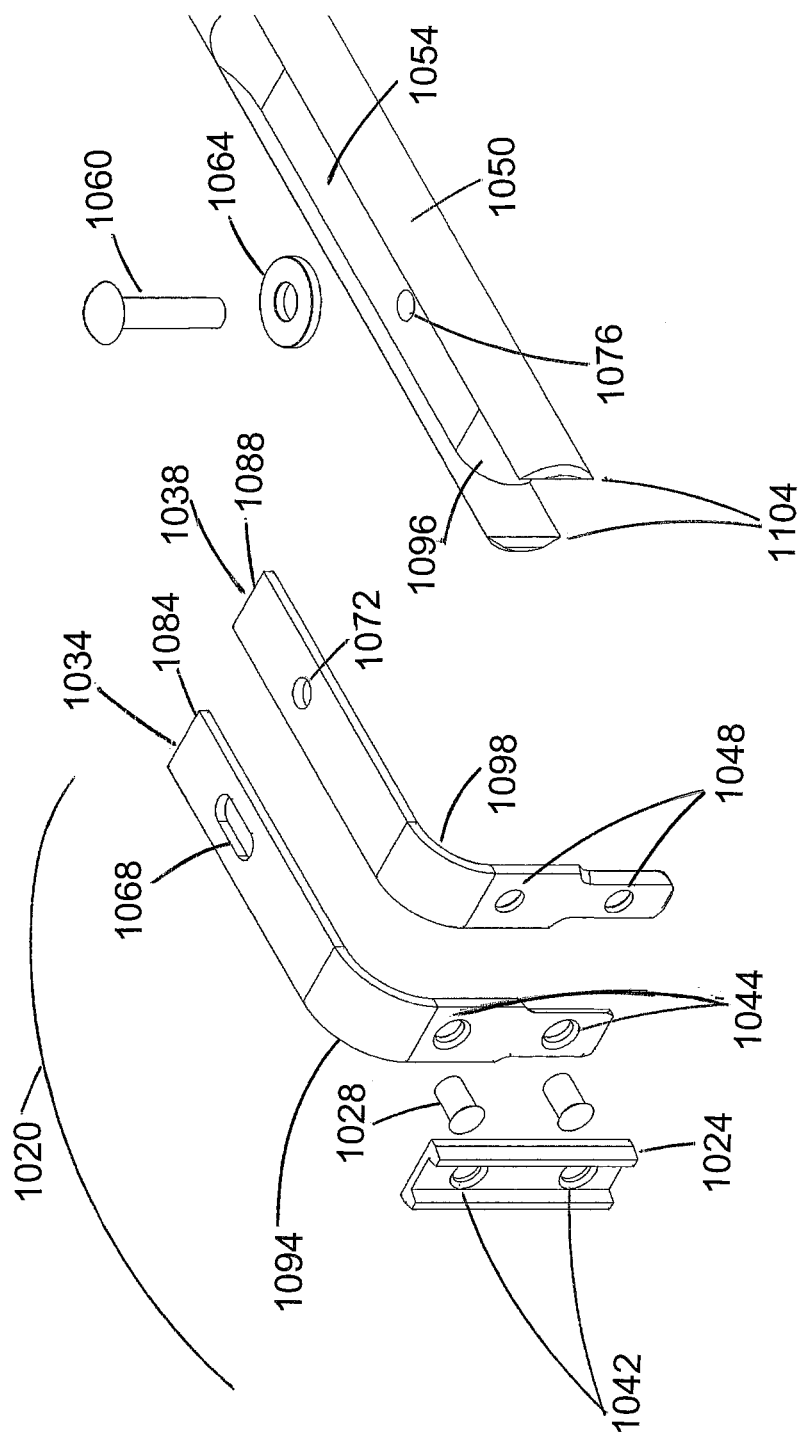
FIG. 15 shows an enlarged and exploded view of the distal end of FIG. 13 with the shaft sheath 1030 (FIG. 13) hidden to expose relevant details.

FIG. 15 shows an enlarged and exploded view of the distal end of FIG. 13 with the shaft sheath 1030 (FIG. 13) hidden to expose relevant details. FIG. 15 has abrading blade 1020 which has abrading head 1024 attachable by one or more head rivets 1028 to distal arm 1034 and proximal arm 1038 through head rivet holes 1042, distal arm rivet holes 1044 and proximal arm rivet holes 1048. The distal arm 1034 and proximal arm 1038 rest within the cutter shaft 1050 in a shaft slot 1054. The distal arm 1034 and proximal arm 1038 are connected to the cutter shaft by a rivet 1060 that passes through washer 1064, blade slot 1068 in distal arm 1034, blade hole 1072 in proximal arm 1038, and into shaft through-hole 1076. One of skill in the art will recognize that the rivets 1028 and 1060 are shown in their manufactured and pre-compressed states.

In a manner analogous to the discussion above in connection with FIG. 4, the upcutter abrading tool 1000 may move the sheath 1030 distally relative to the handle 1012 of the upcutter abrading tool 1000 to effectively withdraw the abrading blade 1020 into a sheathed position so that the sheathed abrading blade 1020 may be inserted through the axial channel 212 (FIG. 7) before deployment within the intervertebral disc space 312.

When the sheath 1030 is moved proximally towards the handle 1012, the abrading blade 1020 becomes unsheathed and shape memory materials used for the distal arm 1034 and the proximal arm 1038 attempt to resume their shape memory shapes. The blade slot 1068 allows relative motion of the longitudinal portion 1084 of distal arm 1034 relative to the longitudinal portion 1088 of the proximal arm 1038.

When unsheathed, the curved portion 1094 of the distal arm 1034 and the curved portion 1098 of the proximal arm 1038 rest against the shaft curvature 1096. Optional shaft extensions 1104 provide lateral support to the abrading blade.

Details on an Abrading Head.

Figure 16:
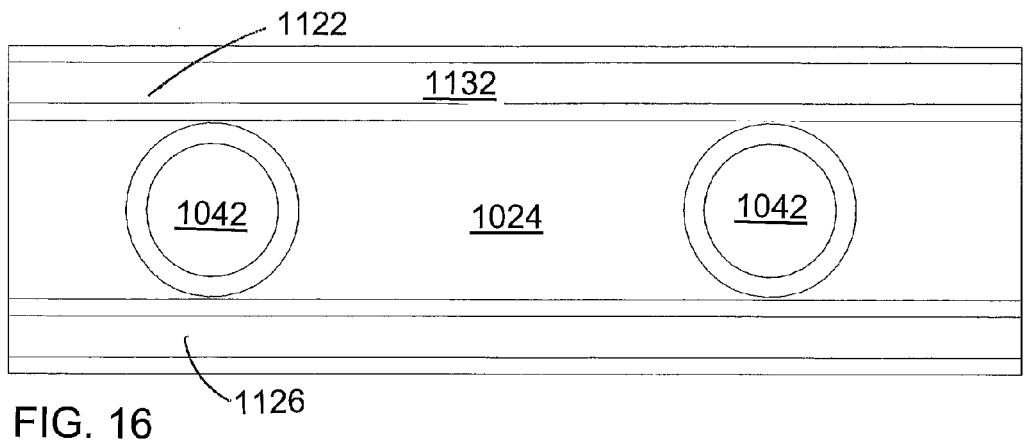
FIG. 16 is a top view of abrading head 1024 shown in FIG. 15.
Figure 17:
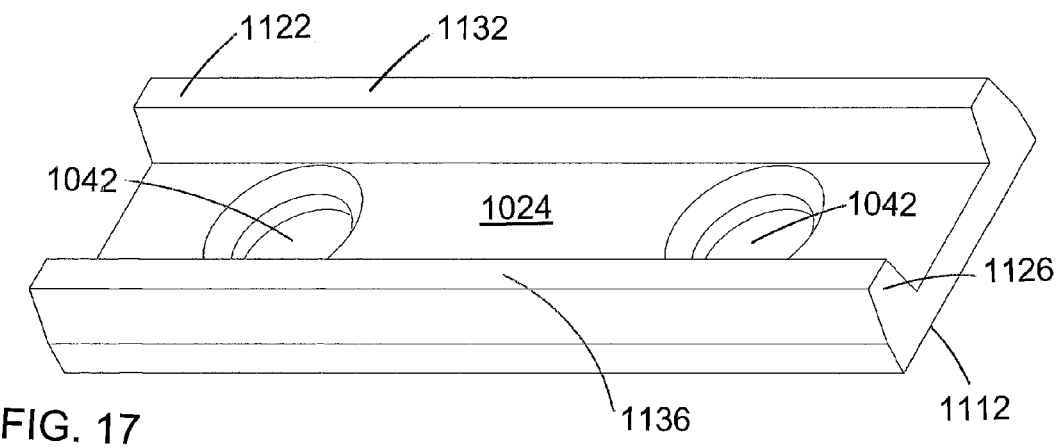
FIG. 17 is a top perspective view of the same abrading head 1024.
Figure 18:
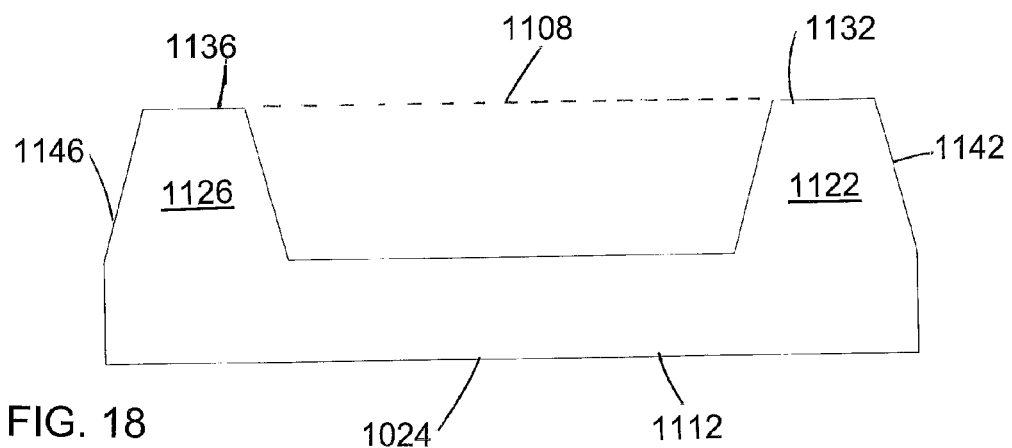
FIG. 18 is an end view of the same abrading head 1024.

FIG. 16 is a top view of abrading head 1024 shown in FIG. 15. FIG. 17 is a top perspective view of the same abrading head 1024. FIG. 18 is an end view of the same abrading head 1024. Head rivet holes 1042 discussed in FIG. 15 are visible in FIGS. 16 and 17.

These figures show that this abrading head 1024 has a pair of rails 1122 and 1126 with distal faces 1132 and 1136. The two distal faces 1132 and 1136 on the two rails 1122 and 1126 are in substantially the same plane (plane 1108) and plane 1108 is substantially parallel with the back face 1112.

Each rail has a sloped leading face 1146 and 1142. There are two leading faces on opposite sides of the abrading head 1024 as one will be a leading face during clockwise rotation of the abrading head 1024 and the other will be the leading face during counterclockwise rotation of the abrading head 1024.

The combined surface area of the two distal faces 1132 and 1136 is relatively small compared with the size of the abrading head 1024 but lacks any cutting edge to cut into the surface of the vertebral endplate. Thus, the surgeon may apply a fair amount of pressure per square inch of contact to effectively and efficiently abrade material from the vertebral endplate including any remaining nucleus pulposus, cartilage, and outer layers of the endplate in order to prepare the endplates for fusion. While the present disclosure is for tools rather than surgical techniques, to provide context it may be useful to know that some procedures performed by some surgeons remove material until the interior surface of both endplates are exposed. Some processes may remove about 1 mm of bone material through the abrading process in order to access the vascular structure within the vertebra. A surgeon will receive feedback on the level of bone being abraded by looking at the material on the abrading head by removing the tool from the surgical site. Flexible cartilage will have one appearance but that would be different from the more granular bone that would be on the tool head after abrading cortical bone. Surgeons may alter the processing based upon a number of factors including an assessment of bone quality of the adjacent vertebrae.

The open area between rails 1122 and 1126 in this example (and 2122 and 2126 in the subsequent example) may channel cut material and thus make the abrading head more efficient in addition to adding certain efficiencies to the manufacturing process. The depth of the rails 1122 and 1126 in this example (and 2122 and 2126 in the subsequent example) help make the abrading heads efficient in removing material. However, as there is a finite total depth to the abrading blade 1020 that can be contained in the cutter shaft sheath 1030, an engineering trade off is made between rail depth and the thickness allocated to other portions of the abrading blade 1020.

As the abrading head 1024 does not change shape when sheathed, the abrading head 1024 does not need to be made of a shape memory material such as Nitinol™ shape memory material. Thus, while abrading head 1024 will generally be selected from biocompatible materials, a wide range of materials are available and may be selected based on a range of factors including ease of machining One material suitable for some applications is 17-4 Stainless Steel.

Partial Advancement of the Cutter Sheath.

Movement of the sheath 1030 away from handle 1012 to sheath the abrading blade 1020 is accomplished by grabbing any portion of the exposed proximal end of the sheath and moving the sheath 1030 relative to the handle 1016. When it is time to unsheathe the abrading blade 1020, the proximal end of the sheath 1030 is moved back towards the handle 1012. This tracks the process described in connection with FIG. 6D and a handle such as shown in FIG. 6 could be used with an abrading head 1024 as is shown in FIGS. 15-18 to perform vertebral endplate preparation on the distal endplate.

Trigger 1016 introduced in FIGS. 13 and 14 provides an option for minor movement of the shaft sheath 1030 to press the distal end of the sheath against a portion of the abrading blade 1020 and thus increase the blade angle.

Range of Blade Angles Needed.

Figure 20:
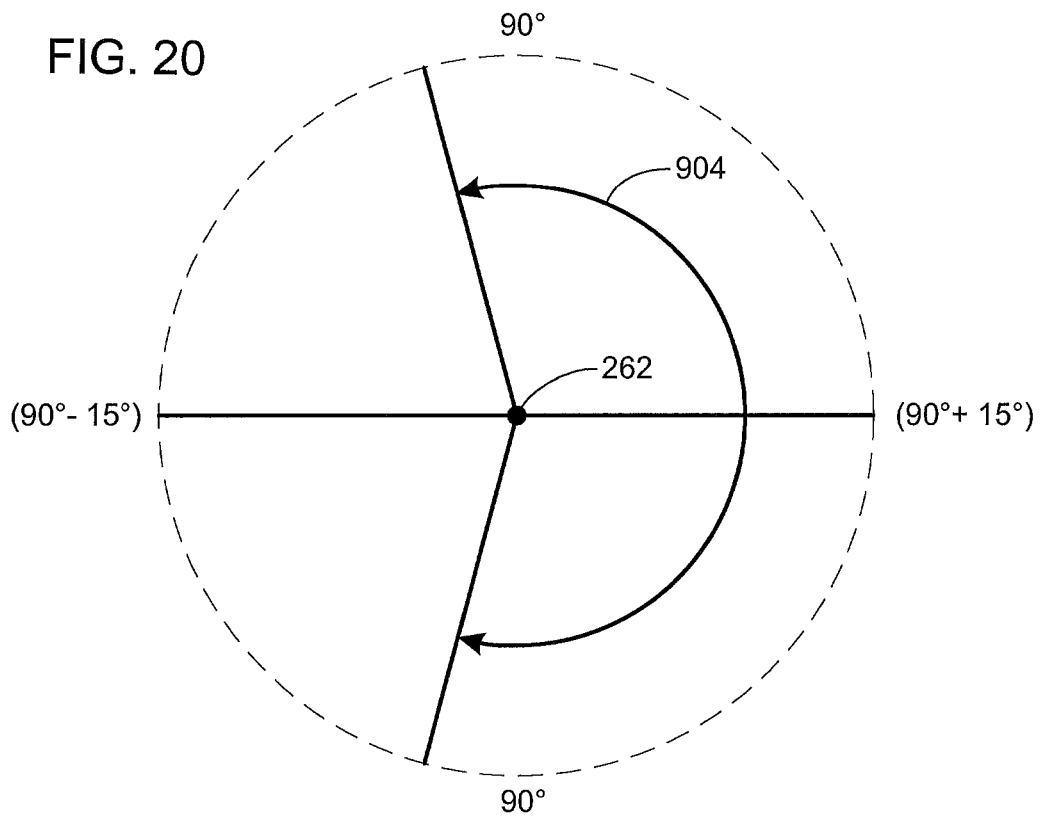
FIG. 20 illustrates that a range of blade angles are needed for preparation 360 degrees around an access channel.
Figure 19:
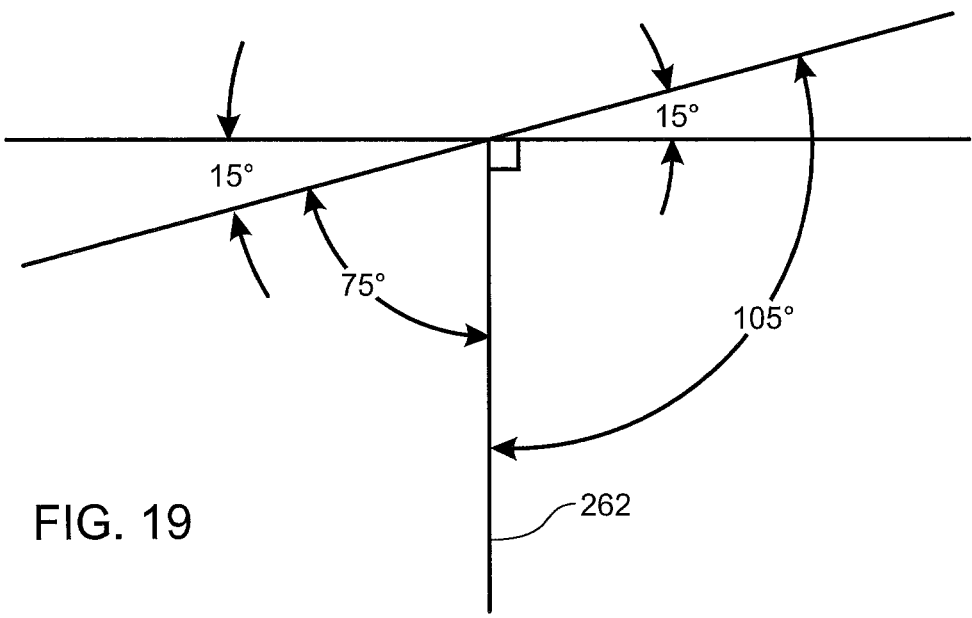
FIG. 19 illustrates a concept of the centerline axis 262 of the cutter shaft 1050 being oblique to a vertebral endplate.

FIG. 19 illustrates a concept of the centerline axis 262 of the cutter shaft 1050 being oblique to the distal endplate (342 in FIG. 7). While an endplate is not going to end exclusively in a uniform plane, there will be some plane that can be said to be representative of the orientation of the endplate. If the endplate plane is 15 degrees from perpendicular, then the blade angle to reach the uphill end will need to be approximately 105 rather than 90 degrees and the blade angle to reach the downhill end will need to be 75 rather than 90 degrees. FIG. 20 highlights something that is not readily apparent in FIG. 19, that is that the angle is continually changing. The optimal blade angle changes in a 360 degree rotation around the centerline axis 262 from a low of 75 degrees up to a high of 105 and back to 75 degrees again.

Given that a tool does not need to be perfectly aligned with the vertebral endplate surface to prepare the vertebral endplate surface adequate for fusion, a tool that could dynamically adjust blade angle 15 degrees could cover a sweep range 904 that is more than half of the 360 degrees needed to prepare the vertebral endplate. A second upcutter abrading tool with an initial blade angle of 75 degrees could be used to prepare the portions of the vertebral endplate using blade angles from 75 to 90 degrees. Note while the terminology for other cutters may be different, in the context of this disclosure, an upcutter works on the distal surface away from the surgeon. Conversely, a down cutter works on the proximal surface. As becomes apparent from consideration of FIGS. 19 and 20, upcutters are needed with default blade angles greater than, less than, and approximately equal to a blade angle of 90 degrees. Likewise, down cutters are needed with default blade angles greater than, less than, and approximately equal to a blade angle of 90 degrees.

Trigger Mechanism.

Figure 21:
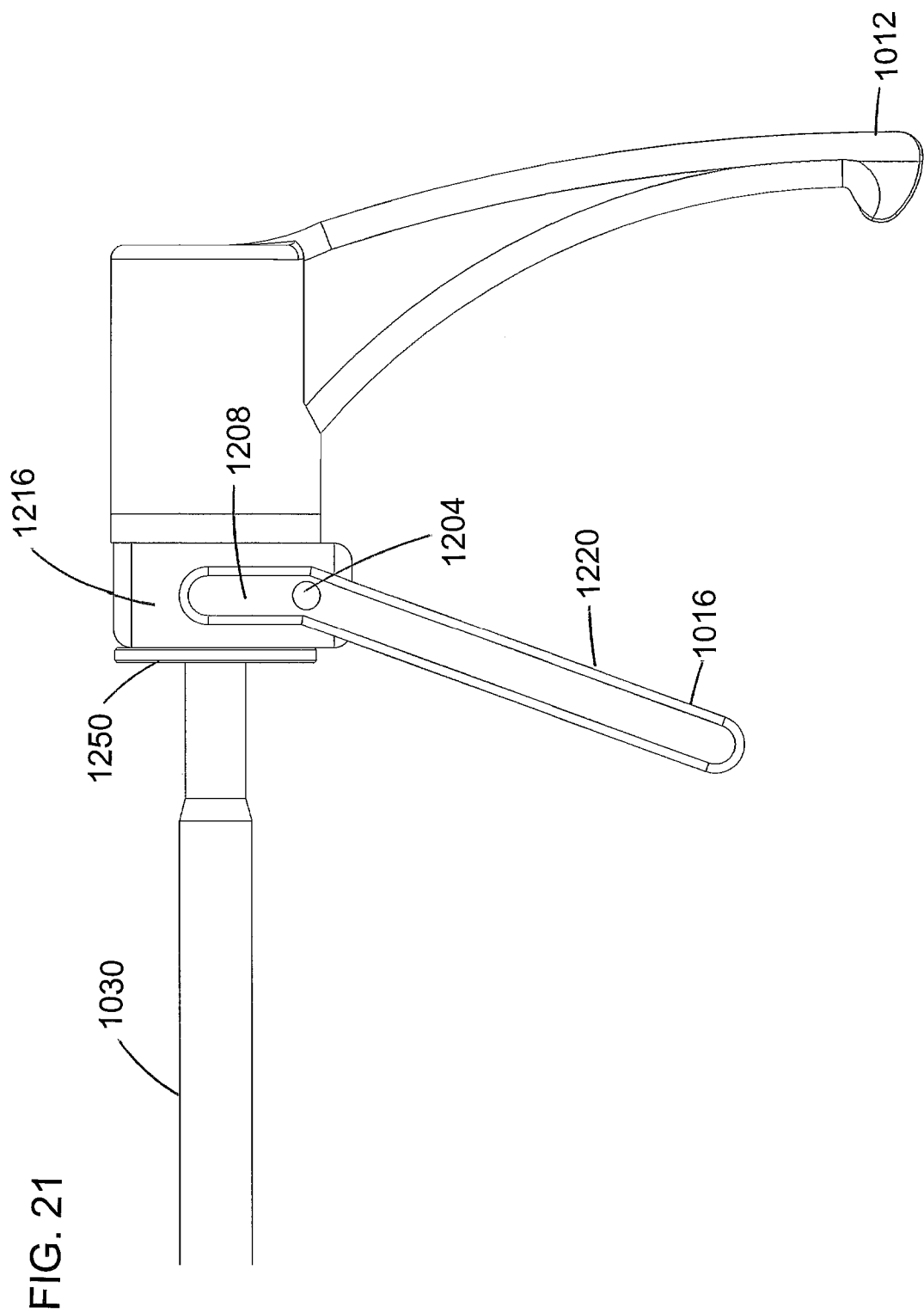
FIG. 21 is an enlarged side view of the proximal end of the upcutter abrading tool.
Figure 22:
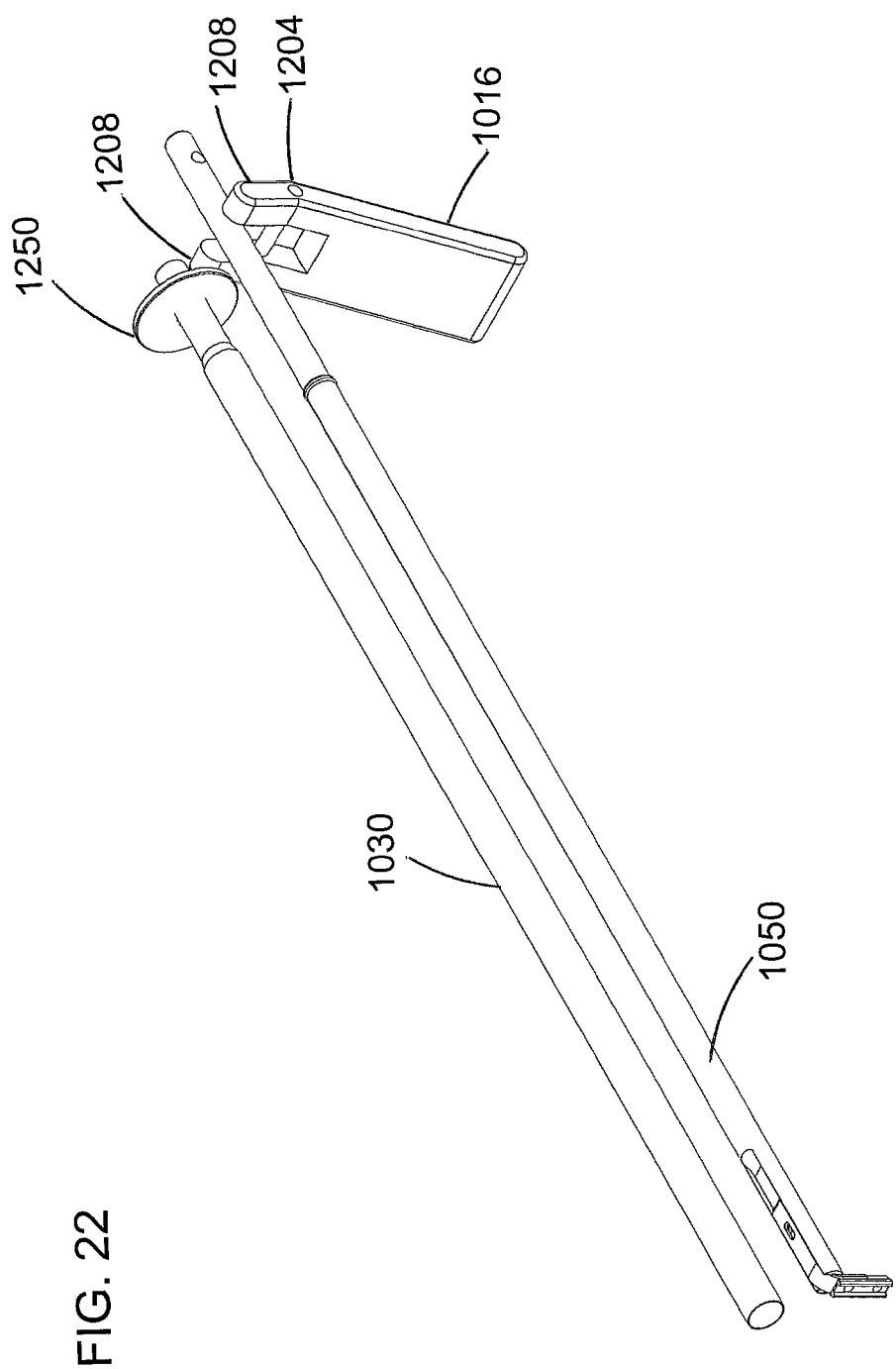
FIG. 22 is a perspective view of the upcutter abrading tool with a series of parts made invisible to focus on the relevant parts and the sheath 1030 placed next to the cutter shaft 1050.
Figure 23:
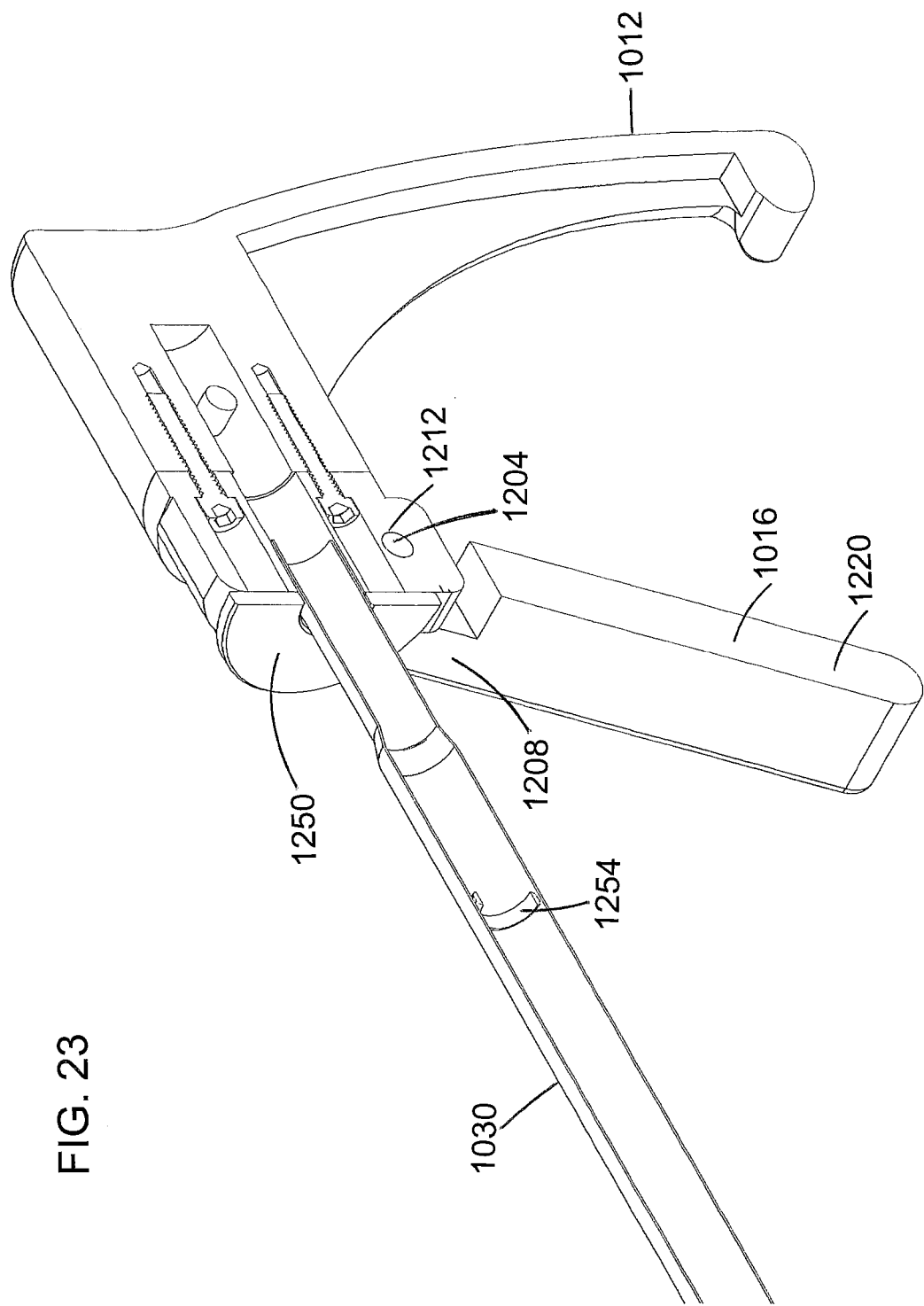
FIG. 23 is a cross section of a perspective view of the proximal end of the upcutter abrading tool 1000 with the cutter shaft 1050 (FIG. 22) made invisible to allow other details to be seen.

The operation of the trigger mechanism can be explained through viewing of three figures. By way of introduction, FIG. 21 is an enlarged side view of the proximal end of the upcutter abrading tool 1000 (FIG. 14). FIG. 22 is a perspective view of the upcutter abrading tool with a series of parts made invisible to focus on the relevant parts and the sheath 1030 placed next to the cutter shaft 1050. FIG. 23 is a cross section of a perspective view of the proximal end of the upcutter abrading tool 1000 with the cutter shaft 1050 (FIG. 22) made invisible to allow other details to be seen.

Trigger 1016 is pinned via trigger pin 1204 that runs through the two trigger arms 1208 and a bore 1212 in trigger mount 1216. One of skill in the art will recognize that the weight of the trigger 1016 would rotate the trigger arms 1208 until they made contact with the sheath flange 1250. So the resting position for the trigger 1016 would be rotated from that shown in this model.

As the trigger lever 1220 is rotated around the trigger pin 1204 towards the handle 1012 the trigger arms 1208 rotate distally and push on the sheath flange 1250 which moves the sheath 1030 distally against friction and eventually the spring force of the shape memory material in distal arm 1034 and proximal arm 1038 (FIG. 15). As the distal end of the shaft sheath 1030 touches the abrading blade 1020 and begins to rotate the blade into a substantially coaxial orientation with the cutter shaft 1050, the blade angle increases. As the surgeon can alter the amount of blade angle by applying different amounts of pressure to the trigger lever 1220, the surgeon can dynamically adjust blade angle to more effectively work the vertebral endplate, especially when the centerline axis 262 (FIGS. 7, 19, and 20) of the cutter shaft 1050 is not perpendicular to the proximal vertebral endplate 342 (FIG. 7).

One of skill in the art will recognize that the flange 1250 could be something other than a washer shape. The flange could be protrusions of any sort that serve to receive pressure from the rotating trigger 1016 and move the sheath 1030 forward against resistance. The flange could be the purposeful use of a wall thickness for the sheath that provides an adequate surface area for the trigger arms to apply pressure directly to the proximal face of the sheath wall.

Cutter Retraction Bumper Stop.

FIG. 23 has the cutter shaft 1050 (FIG. 22) rendered invisible so bumper stop 1254 is visible. Bumper stop 1254 is not relevant to the use of the trigger for dynamic blade angle adjustment but is attached to the cutter shaft 1050 and helps stop the forward movement of the sheath 1030 to prevent the sheath from coming off the cutter shaft 1050 when the sheath 1030 is manually moved to sheath the abrading blade 1020 (FIG. 13)

Down Cutter Abrading Tool.

Figure 24:
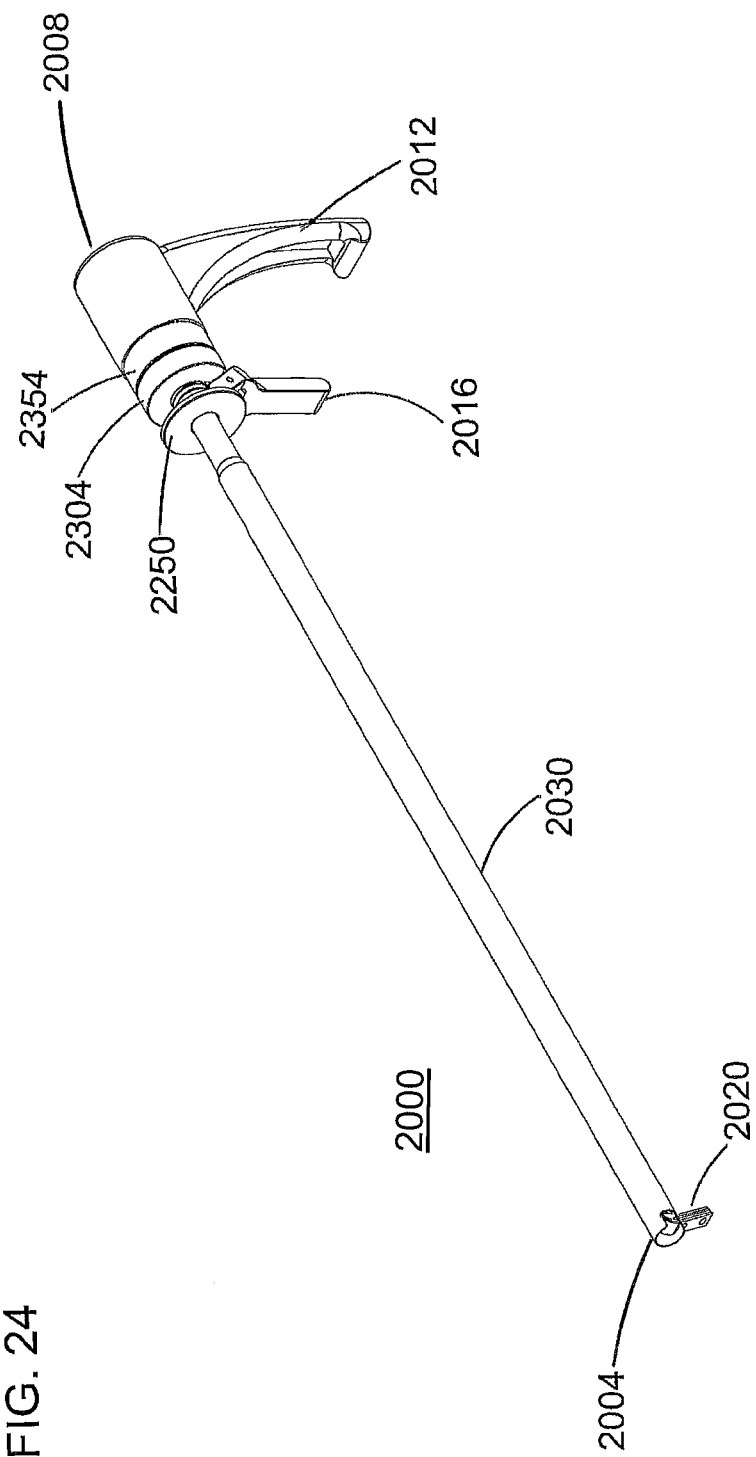
FIG. 24 provides a top perspective view of a down cutter abrading tool 2000.

FIG. 24 provides a top perspective view of a down cutter abrading tool 2000. The down cutter abrading tool 2000 has a distal end 2004 with an abrading blade 2020 intended for insertion via the access channel 212 (FIG. 7) to abrade the cartilage 356 on the endplate of the proximal vertebral body 308 and the proximal vertebral endplate 352.

Down cutter abrading tool 2000 has a proximal end 2008 including a handle 2012 and a trigger 2016. Shaft sheath 2030 is between the distal end 2004 and the proximal end 2008.

Details on an Abrading Blade.

Figure 25:
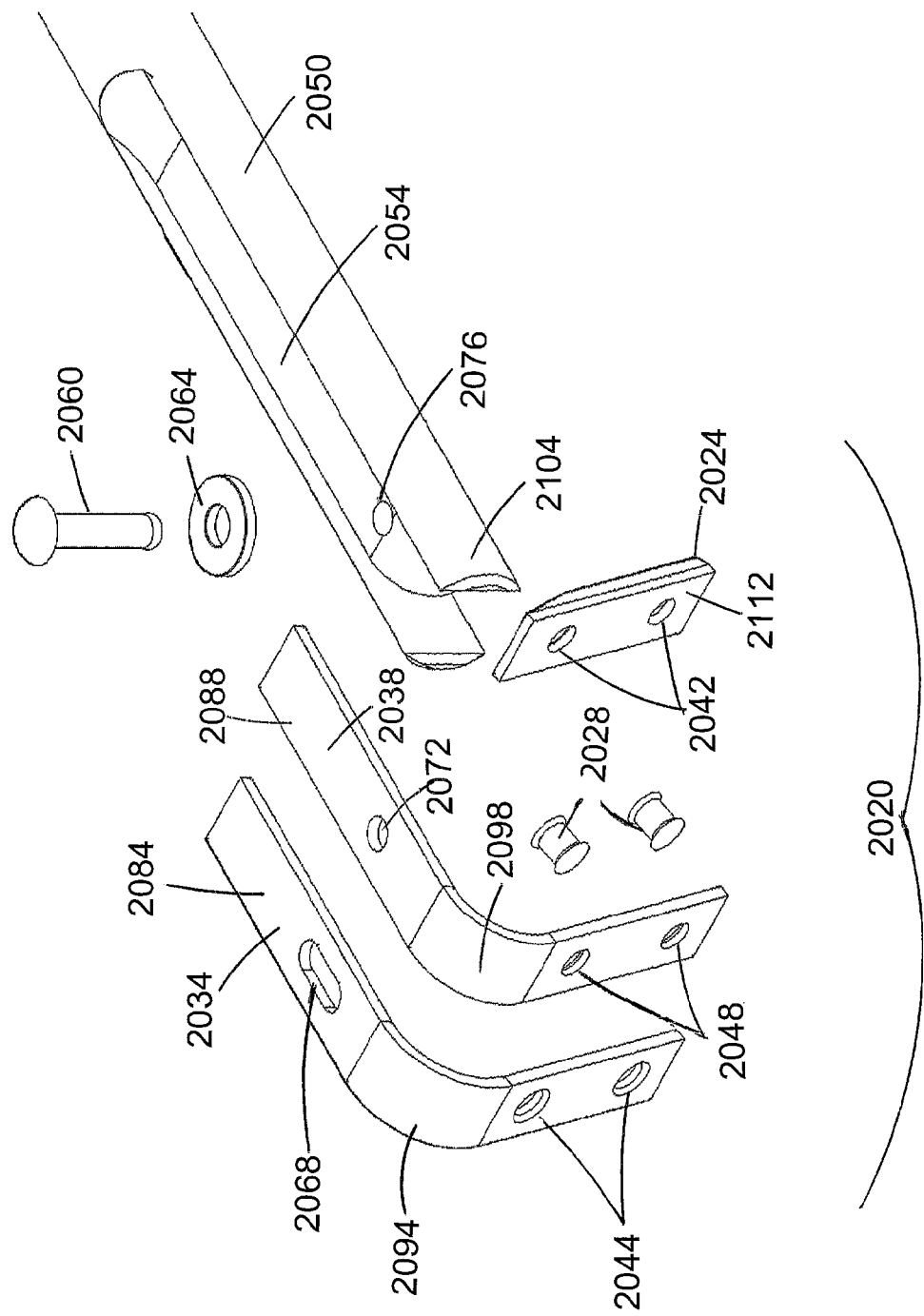
FIG. 25 shows an enlarged and exploded view of the distal end of FIG. 24 with the shaft sheath 2030 (FIG. 24) hidden to expose relevant details.

FIG. 25 shows an enlarged and exploded view of the distal end of FIG. 24 with the shaft sheath 2030 (FIG. 24) hidden to expose relevant details. FIG. 25 has abrading blade 2020 which has abrading head 2024 attachable by one or more head rivets 2028 to distal arm 2034 and proximal arm 2038 through head rivet holes 2042, distal arm rivet holes 2044 and proximal arm rivet holes 2048. The distal arm 2034 and proximal arm 2038 rest within the cutter shaft 2050 in a shaft slot 2054. The distal arm 2034 and proximal arm 2038 are connected to the cutter shaft by a rivet 2060 that passes through washer 2064, blade slot 2068 in distal arm 2034, blade hole 2072 in proximal arm 2038, and into shaft through-hole 2076. One of skill in the art will recognize that the rivets 2028 and 2060 are shown in their manufactured and pre-compressed states.

In a manner analogous to the discussion above in connection with FIG. 4, the down cutter abrading tool 2000 may move the sheath 2030 distally relative to the handle 2012 of the down cutter abrading tool 2000 to effectively withdraw the abrading blade 2020 into a sheathed position so that the sheathed abrading blade 2020 may be inserted through the axial channel 212 (FIG. 7) before deployment within the intervertebral disc space 312.

When the sheath 2030 is moved proximally towards the handle 2012, the abrading blade 2020 becomes unsheathed and shape memory materials used for the distal arm 2034 and the proximal arm 2038 attempt to resume their shape memory shapes. The blade slot 2068 allows relative motion of the longitudinal portion 2084 of distal arm 2034 relative to the longitudinal portion 2088 of the proximal arm 2038.

When unsheathed, the curved portion 2094 of the distal arm 2034 and the curved portion 2098 of the proximal arm 2038 rest against the shaft curvature 2096. Optional shaft extensions 2104 provide lateral support to the abrading blade. While down cutter abrading tool 2000 has a sheath 2030 with a slot as discussed below, a down cutter abrading tool may be implemented using a shaft sheath 1030 as shown in connection with FIG. 13.

Details on an Abrading Head.

Figure 27:
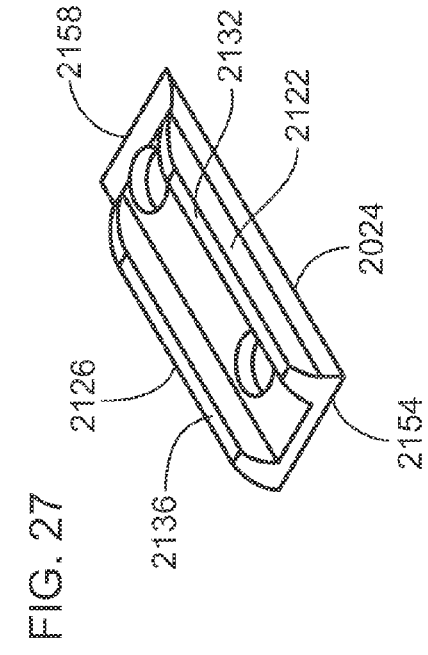
FIG. 27 provides a top perspective view looking at the distal end 2154 of abrading head 2024.
Figure 29:
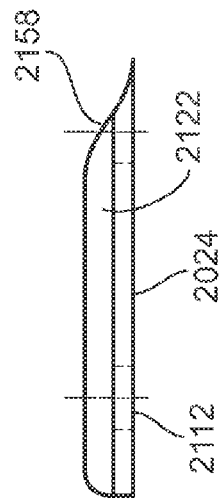
FIG. 29 provides a side view of the abrading head 2024 shown in FIGS. 26-28.
Figure 26:
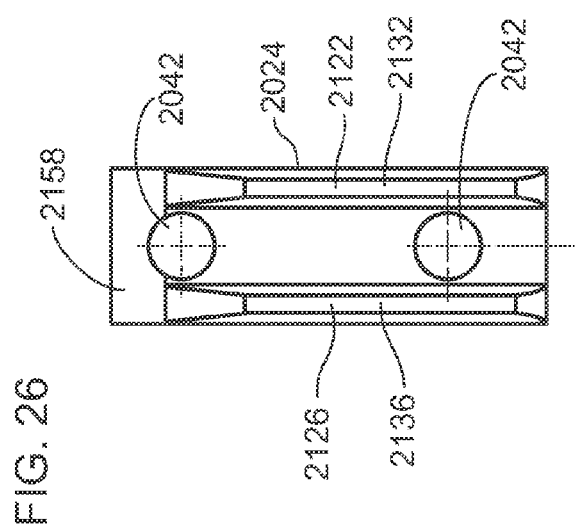
FIG. 26 provides a top view of abrading head 2024.
Figure 28:
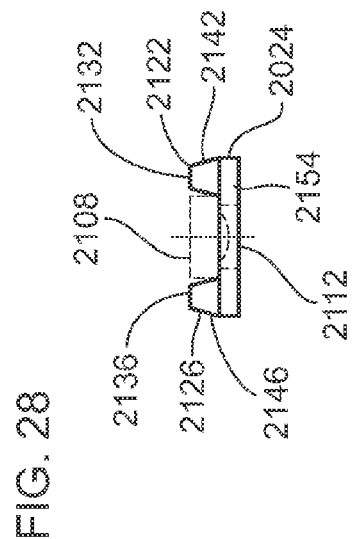
FIG. 28 provides a view of distal end 2154 of abrading head 2024.

FIGS. 26-29 provide four views of an abrading head 2024 adapted for use in a down cutter assembly 2000 (FIG. 24). FIG. 26 provides a top view of abrading head 2024. FIG. 27 provides a top perspective view looking at the distal end 2154. FIG. 28 provides a view of distal end 2154. FIG. 29 provides a side view of the abrading head 2024 shown in FIGS. 26-28. Head rivet holes 2042 discussed in FIG. 25 are visible in FIGS. 26-29.

These figures show that this abrading head 2024 has a pair of rails 2122 and 2126 with distal faces 2132 and 2136 along a portion of each rail. The two distal faces 2132 and 2136 on the two rails 2122 and 2126 are in substantially the same plane (plane 2108) and plane 2108 is substantially parallel with the back face 2112 (best seen in FIG. 25).

Each rail has a sloped leading face 2146 and 2142. There are two leading faces on opposite sides of the abrading head 2024 as one will be a leading face during clockwise rotation of the abrading head 2024 and the other will be the leading face during counterclockwise rotation of the abrading head 2024.

The combined surface area of the two distal faces 2132 and 2136 is relatively small compared with the size of the abrading head 2024 but lacks any cutting edge to cut into the surface of the vertebral endplate. Thus, the surgeon may apply a fair amount of pressure per square inch of contact to effectively and efficiently abrade material from the vertebral endplate including any remaining nucleus pulposus, cartilage, and outer layers of the endplate in order to prepare the endplates for fusion.

One difference between down cutter abrading head 2024 and upcutter abrading head 1024 (FIGS. 16-18) is that the distal end 2154 of abrading head 2024 and the proximal end 2158 of abrading head 2024 are tapered to allow the abrading head 2024 to be moved into the cutter shaft slot 2054 and deployed again as the cutter blade 2020 is sheathed and unsheathed. Proximal end 2158 of abrading head 2024 may be used in connection with a sheath having a blade slot as discussed below. One of skill in the art will recognize that the shape of the proximal end 2158 of the abrading head 2024 used with a sheath slot will need to be compatible with the geometry of the sheath slot and the need to move into and out of the sheath slot as described below.

Abrading head 2024 does not have to be made of a shape memory material. Abrading head 2024 may be made out of a range of biocompatible materials and may be chosen based in part on mechanical properties desired or the ease of machining One suitable material is 17-4 stainless steel.

Use of a Sheath Slot.

Figure 30:
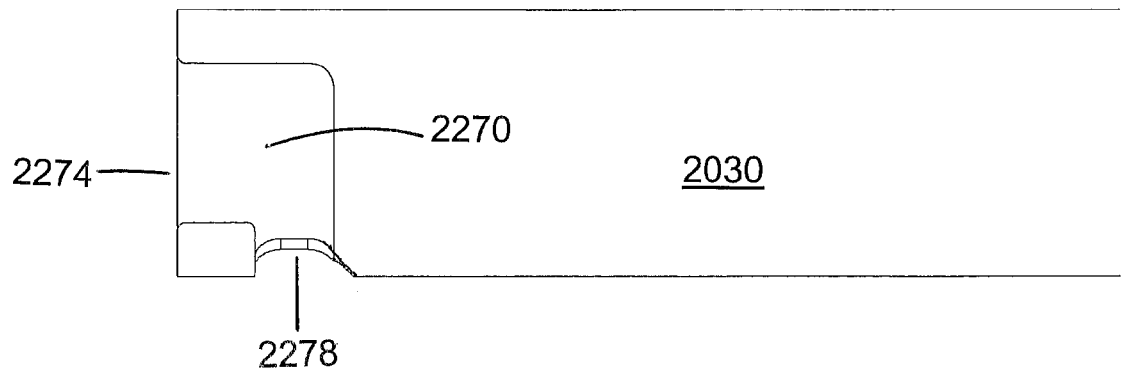
FIG. 30 shows a side view of the distal end of a sheath 2030 with a sheath slot 2270.
Figure 31:
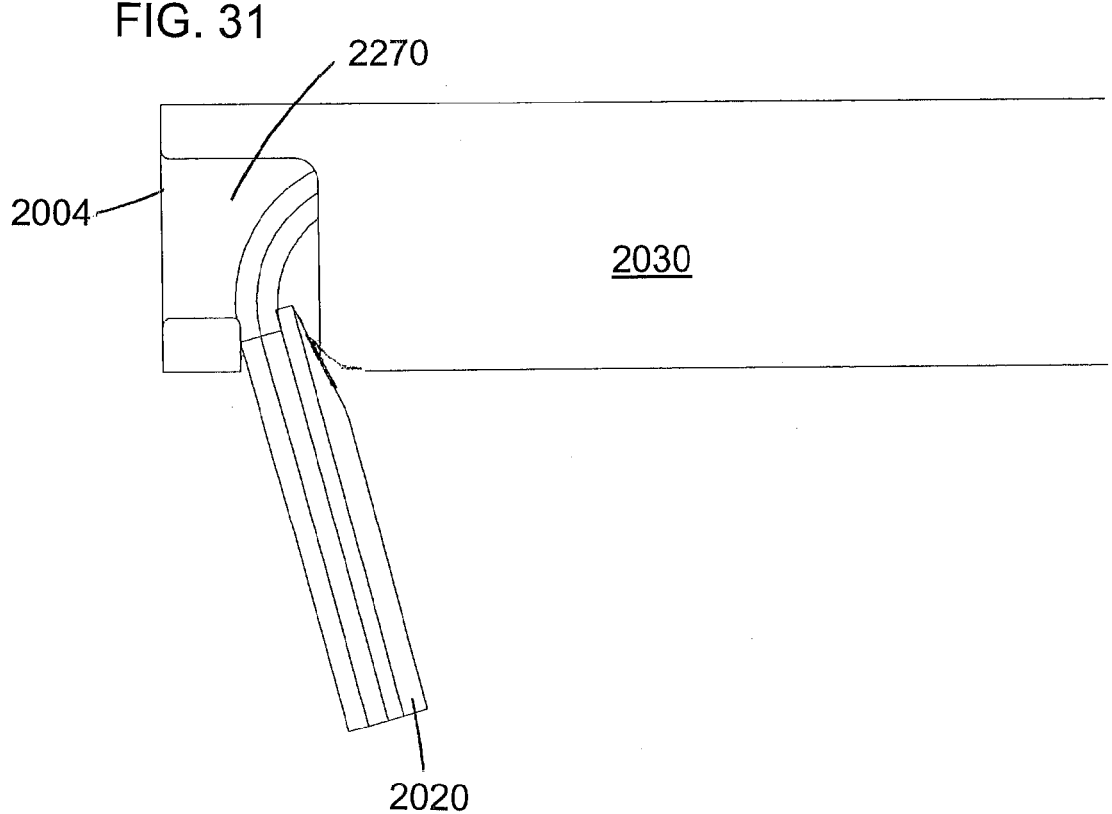
FIG. 31 shows a side view of the distal end of a shaft sheath 2030 with a sheath slot 2270 as shown in FIG. 30 but includes an abrading blade 2020 captured in the axial slot 2274.

FIGS. 30 and 31 show two side views of the distal end of a sheath 2030 with a sheath slot 2270. The sheath slot 2270 has two sections, an axial slot 2274 open at the distal end 2004 of the sheath and a radial slot 2278 open to the axial slot 2274. FIG. 31 includes an abrading blade 2020 captured in the axial slot 2274. The operation of the sheath slot is summarized in FIG. 32. for process 3000. Turning now to FIG. 32—

Step 3010—Deliver the sheathed abrading blade 2020 to the surgical site.

Step 3020—Unsheathe the sheathed abrading blade 2020 to allow the abrading blade to assume its default blade angle as the abrading blade extends out of the axial slot 2274 portion of the sheath slot 2270.

Step 3030—Rotate the sheath 2030 relative to the handle 2012 (FIG. 24) to capture the abrading blade 2020 within the radial slot 2278 portion of the sheath slot 2270. The sheath slot could be implemented to have a slightly larger opening at the beginning of the radial slot to facilitate placement of the abrading blade 2020 but this is not required in all implementations.

Step 3040—Use abrading blade. This may include altering the blade angle by moving the sheath 2030 relative to the pinned end of the abrading blade 2020 (see rivet 2060 and exploded components in FIG. 25). The sheath 2030 may be moved through use of a threaded mechanism (such as the one discussed below) or through the use of a dynamic blade angle change such as through a trigger that temporarily pushes the sheath in a distal direction. While the blade angle may be purposefully increased, the use of the sheath slot 2270 resists or at least reduces any inadvertent increase in blade angle from contact with tissue while using the abrading blade to exert force in a proximal direction.

Step 3050—Release abrading blade from the radial slot 2278 portion of the sheath slot 2270 by rotating the sheath 2030 in the opposite direction from step 3030.

Step 3060—Move the sheath 2030 distally relative to the handle 2012 to sheathe the abrading blade 2020.

Step 3070—Withdraw the sheathed abrading blade 2020 from the surgical site.

Threaded Advancement of Cutter Sheath.

FIGS. 24, 33, 34, and 35 show a yoke assembly that is used to move the initial position of the trigger 2016 relative to the sheath flange 2250 so as to impose a static position on the cutter sheath 2030 that remains without the ongoing application of pressure by the surgeon (as opposed to the dynamic movement of the cutter sheath in response to the imposition of force through use of the trigger 2016).

Figure 33:
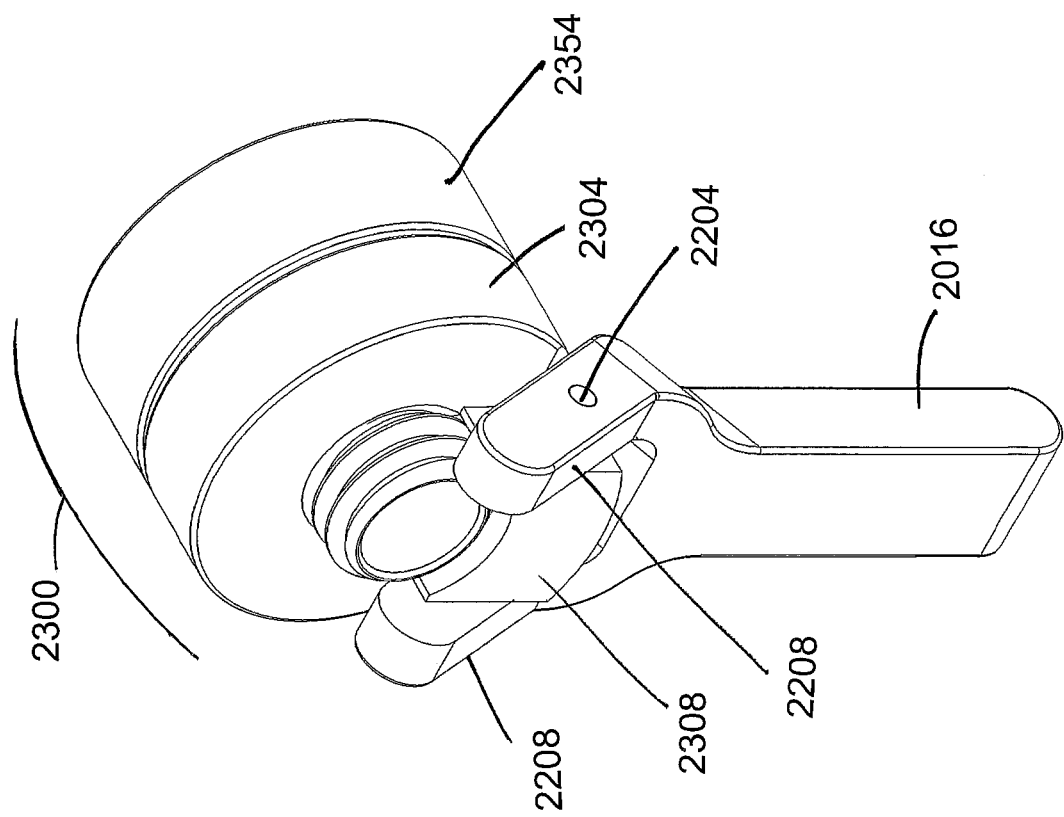
FIG. 33 provides an enlarged perspective view of just the trigger 2016 and the yoke assembly 2300.
Figure 34:
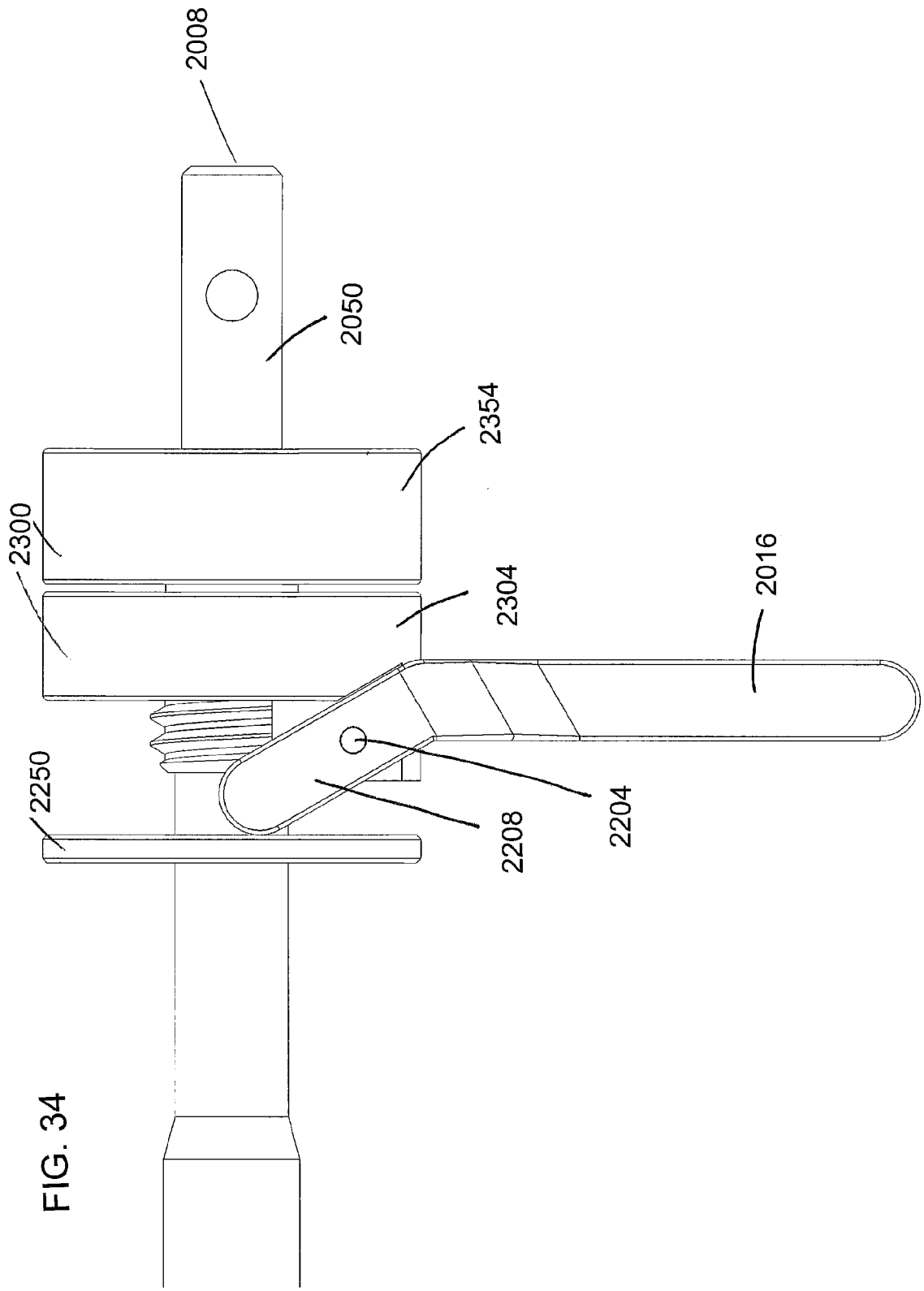
FIG. 34 provides an enlarged side view of the proximal end 2008 of the down cutter assembly 2000. In order to highlight relevant components, handle 2012 (FIG. 24) has been made invisible.
Figure 35:
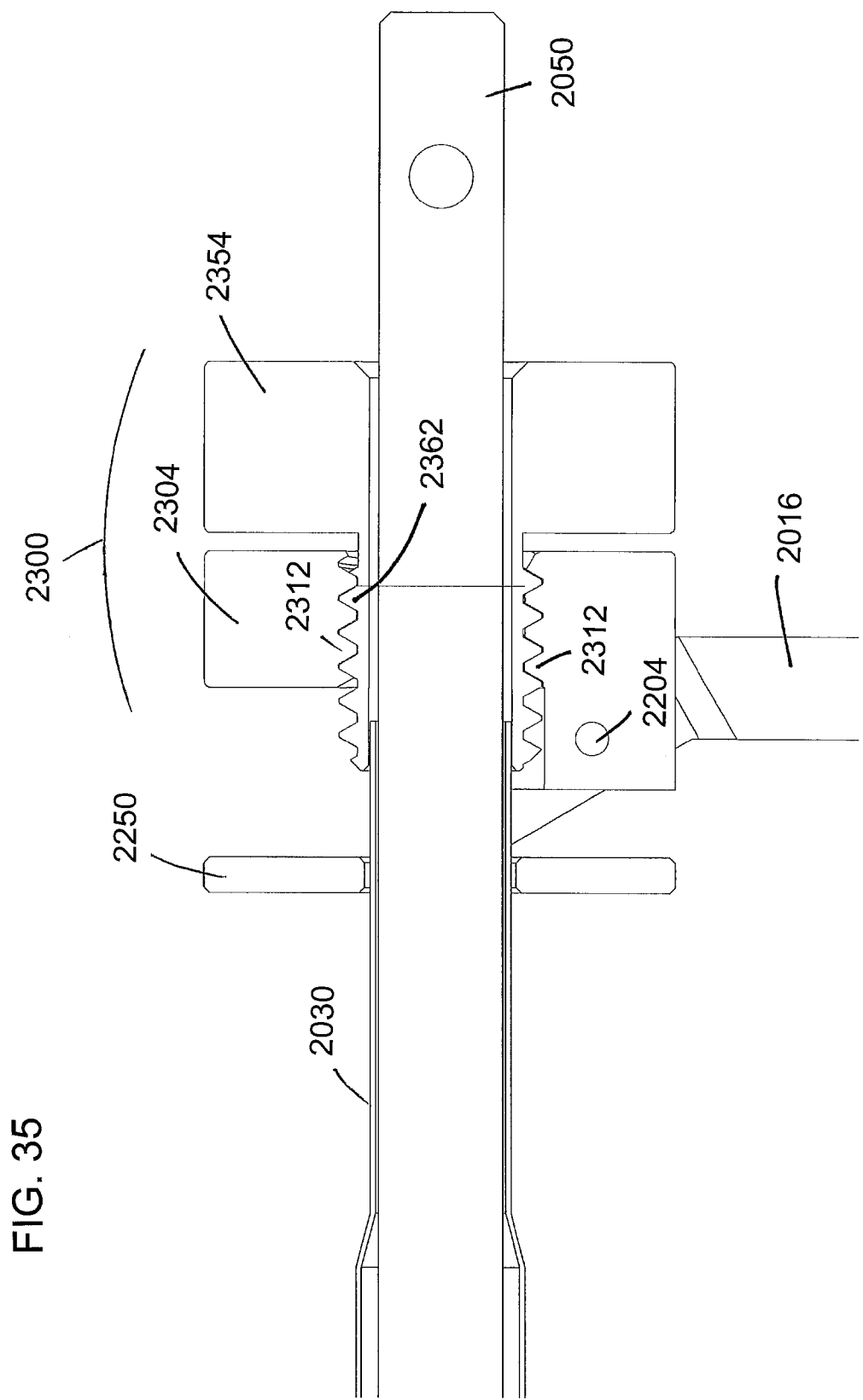
FIG. 35 is a cross section of FIG. 34.

FIG. 24 provides a perspective view of the down cutter 2000. FIG. 33 provided an enlarged perspective view of just the trigger 2016 and the yoke assembly 2300. FIG. 34 provides an enlarged side view of the proximal end 2008 of the down cutter assembly 2000. In order to highlight relevant components, handle 2012 (FIG. 24) has been made invisible. FIG. 35 is a cross section of FIG. 34.

Viewing FIGS. 33, 34, and 35, the yoke assembly 2300 has a female yoke piece 2304 which has trigger mounting section 2308. Trigger pin 2204 passes through bores in both trigger arms 2208 and trigger mounting section 2308 of the female yoke piece 2304. Thus the trigger can pivot relative to the position of the trigger mounting section 2308 to apply force on the sheath flange 2250.

The position of the trigger mounting section 2308 may be moved relative to the sheath flange 2250 by rotating male yoke piece 2354. Rotation of male yoke piece 2354 causes male threads 2362 to rotate relative to female threads 2312 in female yoke piece 2304 to move female yoke piece 2304 along the cutter shaft 2050. Movement of the female yoke piece 2304 causes the trigger arms 2208 to contact and advance the sheath flange 2250. The advancement remains static until augmented by additional advancement caused by rotation of the trigger 2016 to rotate the trigger arm 2208 in the distal direction or until the male yoke piece 2354 is rotated again (either an additional amount in the first direction or rotated back until the trigger arms 2208 are no longer causing an alteration in blade angle of the abrading blade 2020).

One of skill in the art will recognize that the yoke assembly modeled in order to convey the concepts of interest would need an extended threaded interface between the male and female threads in order to achieve the extent of movement necessary to advance the sheath flange sufficiently to alter the blade angle. This modification is easily made by one of skill in the art after review of this disclosure.

Combinations, Variations, and Alternatives.

While the upcutter abrading tool (1000 in FIG. 13) illustrated both the upcutter abrading head 1024 and the trigger mechanism for advancing the sheath to dynamically alter blade angle, these innovations may be applied separately. One of skill in the art will appreciate that an upcutter abrading head may be used in a tool without a trigger but uses a handle such as shown in FIGS. 4A and 4B.

One of skill in the art will appreciate that a trigger mechanism to dynamically alter blade angle could be implemented in a cutter tool that uses a closed loop cutter blade such as blade 453 (FIG. 5B) or a thin blade such as blade 800 (FIG. 10).

Down cutter abrading tool 2000 (FIG. 24) illustrated:
A) a down cutter abrading head,
B) the use of a trigger for dynamic blade angle adjustment,
C) the use of a threaded mechanism for static changes to blade angle, and
D) the use of a sheath slot for resisting changes to blade angles.

One of skill in the art will appreciate that a down cutter abrading head could be implemented in a cutter like cutter 400 introduced in FIG. 3 without the other improvements shown in down cutter abrading tool 2000. Conversely, one of skill in the art will appreciate that a wide range of tool heads including blades other than an abrading head could be used in a down cutter tool analogous to down cutter abrading tool 2000. The blade could be a closed loop blade with such as shown in FIG. 8 with a wide range of blade angles including blade angles less than and greater than approximately 90 degrees. The blade could be a thin blade such as shown in FIGS. 9-12, again in a wide range of blade angles.

One of skill in the art will appreciate that use of a trigger for dynamic blade angle adjustment could be implemented in a cutter like cutter 400 introduced in FIG. 3 without the other improvements shown in down cutter abrading tool 2000. Conversely, one of skill in the art will appreciate that the down cutter abrading tool 2000 could be implemented without a trigger for dynamic adjustment of blade angle. The use of a trigger for dynamic adjustment to blade angle could be used with a variety of tool heads including blades such as a closed loop blade as shown in FIG. 8 or a thin blade such as shown in FIGS. 9-12. The blade angle for the tool head could be more, less, or close to approximately 90 degrees.

One of skill in the art will appreciate that a threaded mechanism for advancing the sheath to make a static alteration in blade angle could be implemented in a cutter like cutter 400 introduced in FIG. 3 without the other improvements shown in down cutter abrading tool 2000. Specifically, a cutter could be implemented that uses a threaded mechanism to alter blade angle but without a mechanism for dynamic alteration of blade angle such as the trigger mechanisms discussed above. Likewise, a threaded mechanism for alteration of blade angle could be used with a variety of tool heads including blades such as a closed loop blade as shown in FIG. 8 or a thin blade such as shown in FIGS. 9-12. The blade angle for the tool head could be more, less, or close to approximately 90 degrees.

One of skill in the art will appreciate that the use of a sheath slot to resist alteration of blade angle that would arise from an extended down cutter blade of any type making contact with a proximal endplate can be implemented in a wide range of cutters including a cutter like that shown in FIG. 4. Likewise, a sheath slot for resisting changes to blade angle could be used with a variety of tool heads including blades such as a closed loop blade as shown in FIG. 8 or a thin blade such as shown in FIGS. 9-12. The blade angle for the tool head could be more, less, or close to approximately 90 degrees. Typically, a sheath slot will be of use for a tool that works on the proximal endplate rather than the distal endplate but a tool that works on both the proximal and distal endplate could benefit from a sheath slot.

Preliminary and Finishing Abrading Tools.

While the two abrading heads 1024 and 2024 discussed above may be suitable for rough and final preparation of endplates, one could implement teachings from the present disclosure using a set of preliminary abrading heads that have narrower but deeper rails than shown in abrading heads 1024 and 2024 followed by finishing abrading tools having broader but shallower rails than shown in abrading heads 1024 and 2024.

Alternative Rails.

FIG. 36 repeats an end view of abrading head 1024 as described in FIG. 18. FIG. 36 shows an abrading head 1024 that has a pair of rails 1122 and 1126 with distal faces 1132 and 1136. The two distal faces 1132 and 1136 on the two rails 1122 and 1126 are in substantially the same plane (plane 1108) and plane 1108 is substantially parallel with the back face 1112. One could make a variant (not shown) of the abrading head 1024 that connects the two rails to essentially form a picture frame using the two rails as two sides of the picture frame.

In FIG. 36 each rail has a sloped leading face 1146 and 1142. There are two leading faces on opposite sides of the abrading head 1024 as one will be a leading face during clockwise rotation of the abrading head 1024 and the other will be the leading face during counterclockwise rotation of the abrading head 1024.

FIG. 37 shows an end view of an abrading head 2404 with substantially perpendicular faces 2408 and 2412. FIG. 37 shows an abrading head 2404 that has a pair of rails 2416 and 2420 with distal faces 2424 and 2428. The two distal faces 2424 and 2428 on the two rails 2416 and 2420 are in substantially the same plane (plane 1108) and plane 1108 is substantially parallel with the back face 1112.

FIG. 38 shows an end view of an abrading head 2444 with a single rail 2448 and a single face 2452 in plane 1108 which is substantially parallel with back face 1112. If abrading head 2444 is connected to the blade arms by one or more rivets, the single face 2452 would need head rivet holes analogous to the head rivet holes 1042 in FIG. 17.

FIG. 39 shows an end view of an abrading head 2464 that has a pair of rails 2468 and 2472 with distal faces 2476 and 2480. The two distal faces 2476 and 2480 on the two rails 2468 and 2472 are in substantially the same plane (plane 1108) and plane 1108 is substantially parallel with the back face 1112. Note that if the saw-tooth profile comes to a point for each of the two rails 2468 and 2472, then the distal faces 2476 and 2480 will be lines at the apexes of the saw-tooth profiles. Another way of expressing the concept is that in some implementations only the crest lines of the rails will be in plane 1108.

While the abrading head 1024 may work best for some applications, there may be reasons to prefer a choice from abrading heads 2404, 2444, 2464, or some hybrid of these abrading heads for some applications.

While these variations in rail profile have been discussed in the context of an upcutter abrading head, one of skill in the art will recognize that these rail profiles may be used in a down cutter abrading head analogous to abrading head 2024 shown in FIGS. 26-29.

Structures Providing Means for Various Functions.

For the convenience of the reader, it is useful to summarize some of the teachings set forth above by mapping specific structures to means for performing specific functions. Unless otherwise required by local practice, these examples are not intended to be either exhaustive or limiting but to be illustrative of generalized teachings of this disclosure.

A means for retracting and extending an abrading blade includes the attachment of the blades to the cutter shaft as set forth above and the ability of the relative motion of the cutter sheath relative to the cutter shaft and the attached abrading blade to effectively alter the blade angle of the abrading blade to reduce the profile of the cutter assembly. The means include the use of shape memory material to have an unsheathed blade resume a particular blade angle.

The rails on the various abrading heads provide an example of a means to abrade. The abrading heads disclosed throughout this document may also be described as a means to promote bleeding of vertebrae endplates.

The trigger mechanisms and the interaction with the cutter sheaths provide an example of a means for dynamic alteration of blade angle. One of skill in the art can understand that other mechanisms are possible for the dynamic alteration of blade angle. For example, a cutter tool constructed without a sheath could use a pair of half shafts that are keyed or otherwise connected together. In one implementation, the top half shaft would be connected to the handle at the proximal end and have a connection to the blade at the distal end much in the manner as described above. The lower shaft would be able to extend out distally to alter the blade angle not just for alteration during use but also to a more severe alteration to place the blade angle so close to 180 degrees that the cutter tool with connected cutter blade could be removed through a constrained channel. For example the distal end of the cutter tool may need to fit through a cross section of about 9 mm. This sheath-less cutter tool could have one or more mechanisms for a static alteration of blade angle in addition to a means for dynamic alteration of blade angle. One mechanism for static alteration of blade angle might be used to move the blade head to a position for movement to or from the surgical site. Another mechanism for static alteration may be used to make fine adjustments to the resting position blade angle of the blade head.

The threaded yoke and the interaction with the sheath provides an example of a static alteration of blade angle in that the alteration remains in place until affirmatively changed, as opposed to the dynamic alterations of blade angle that remain in effect only as long as there is continued effort to maintain the alteration.

Dynamic alteration of blade angle and static alteration of blade angle are both part of a more general concept of means for alteration of a blade angle.

One of skill in the art will recognize that the static alteration of blade angle could be adapted to use other mechanisms known in the art. One example would be to use a ball detent with the ball on the sheath and the detent on the shaft. Another example would be to use a rack and pinion with a rack gear on the shaft and a mechanism in the handle that actuates a pinion gear to move the shaft based on rotation of the pinion gear and then hold the pinion gear in place to maintain the position of the shaft.

The sheath slot and the capacity to engage the abrading blade (or other blade assembly) with the sheath slot is an example of a means for maintaining blade angle.

One of skill in the art will recognize that some of the alternative implementations set forth above are not universally mutually exclusive and that in some cases additional implementations can be created that employ aspects of two or more of the variations described above. One of skill in the art may find it advantageous to take one or more innovative aspects of an implementation set forth above without implementing all the innovative aspects of that implementation or in combining innovations from this disclosure with other systems, methods, or apparatus. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art.

The legal limitations of the scope of the claimed invention are set forth in the claims that follow and extend to cover their legal equivalents. Those unfamiliar with the legal tests for equivalency should consult a person registered to practice before the patent authority which granted this patent such as the United States Patent and Trademark Office or its counterpart.

What is claimed is:

1. A cutter for disrupting material in an intervertebral space between an endplate on a cephalad vertebral body and an endplate on an adjacent but more caudal vertebral body, the cutter comprising:
    a cutter shaft having a long axis;
    a cutter sheath surrounding at least a portion of the cutter shaft, the cutter sheath being a confined component of the cutter when assembled;
    a cutter blade comprising shape memory material; the cutter blade configured to be at least partially retracted into and extended from the cutter sheath, the shape memory material in the cutter blade adapted to assume a position with a default blade angle at least partially transverse to the long axis of the cutter shaft, the default blade angle assumed when an only constraint on the cutter blade is a connection to the cutter shaft, the default blade angle measured between a midline of the cutter blade when unsheathed and the long axis of the cutter shaft; and
    a sheath slot near a distal end of the cutter sheath so that the cutter blade when unsheathed may be positioned within the sheath slot so that a portion of the cutter sheath resists movement by the cutter blade to increase a current blade angle for the cutter blade positioned within the sheath slot;
    wherein the sheath slot is comprised of
        an axial slot open at a distal end of the cutter sheath; and
        a radial slot open to the axial slot.

2. The cutter of claim 1 wherein the cutter is adapted to extend through an axial bore along an axis extending through at least the endplate on the adjacent but more caudal vertebral body to position one end of the cutter into the intervertebral space.

3. The cutter of claim 1 wherein the cutter has a trigger mechanism to dynamically alter the current blade angle.

4. The cutter of claim 1 wherein the cutter blade is configured to abrade an endplate.

5. The cutter of claim 1 wherein the cutter blade is configured to disrupt nucleus material.

6. The cutter of claim 1 wherein the cutter blade is a down cutter.

7. A cutter for disrupting material in an intervertebral space between an endplate on a cephalad vertebral body and an endplate on an adjacent but more caudal vertebral body, the cutter comprising:
    a cutter shaft having a long axis;
    a cutter sheath surrounding at least a portion of the cutter shaft, the cutter sheath being a confined component of the cutter when assembled;
    a cutter blade; the cutter blade configured to be at least partially retracted into and extended from the cutter sheath, the cutter blade when extended at least partially transverse to the long axis of the cutter shaft; the cutter blade made at least in part from a shape memory material;
    a blade angle of the cutter blade measured between a midline of the cutter blade when extended and the long axis of the cutter shaft; and
    a mechanism for moving the cutter sheath relative to the cutter blade and to overcome a spring force from the shape memory material in the cutter blade to alter the blade angle of the cutter blade.

8. The cutter of claim 7 wherein the mechanism for moving the cutter sheath includes:
    a flange extending from the cutter sheath along a portion of the cutter sheath that is not placed within an axial bore; and
    a mechanism for imparting force onto the flange to move the flange from an initial flange position assumed after extension of the cutter blade from the cutter sheath, wherein the flange moves along a direction of the long axis of the cutter shaft to cause an alteration of an extension angle of the cutter blade.

9. The cutter of claim 8 wherein the mechanism for imparting force onto the flange is a lever that pushes the flange towards a distal end of the cutter so that the cutter sheath pushes the cutter blade to alter the extension angle.

10. The cutter of claim 8 wherein the mechanism for imparting force onto the flange is a threaded element adapted to alter a distance between the flange and a proximal end of the cutter.

11. The cutter of claim 8 wherein the mechanism for imparting force onto the flange includes a rack and pinion.

12. The cutter of claim 8 wherein the mechanism for imparting force onto the flange includes a ball and detent mechanism.

13. An abrading tool for abrading an endplate of a vertebra, the abrading tool comprising:
    a cutter shaft with
        a longitudinal axis;
        a distal end of the cutter shaft; and
    an abrading blade with an abrading blade head attached to
        a distal end of the cutter shaft;
    a means for retracting and extending the abrading blade to allow the abrading blade to be retracted at least partially into a sheath for delivery into an intervertebral disc space; a cutter sheath surrounding at least a portion of the cutter shaft, the cutter sheath being a confined component of the cutter when assembled;
    a means for alteration of blade angle to blade angles greater than and less than 90 degrees; and
    a handle at a proximal end of the cutter shaft.

14. The abrading tool of claim 13 wherein the means for alteration of blade angle uses a means for dynamic alteration of blade angle.

15. The abrading tool of claim 13 wherein the means for alteration of blade angle uses a means for static alteration of blade angle.

16. The abrading tool of claim 15 wherein the means for alteration of blade angle uses a means for static alteration of blade angle in addition to the means for dynamic alteration of blade angle.

17. The abrading tool of claim 13 for abrading an endplate of a vertebra wherein the abrading blade has a means to promote bleeding of vertebrae endplates.

18. The abrading tool of claim 17 wherein the abrading blade is adapted for use to abrade a vertebral endplate to promote controlled bleeding of the vertebral endplate without compromising a structural integrity of the vertebral endplate.

19. The abrading tool of claim 18 wherein the abrading blade is adapted for a removal of cartilage from the vertebral endplate.

20. The abrading tool of claim 13 for abrading an endplate of a vertebra wherein the abrading tool is configured as an upcutter.

21. The abrading tool of claim 13 for abrading an endplate of a vertebra wherein the abrading tool is configured as a down cutter.

22. The abrading tool of claim 13 for abrading an endplate of a vertebra further comprising a sheath slot near a distal end of the cutter sheath so that the abrading blade when extended may be positioned within the sheath slot so that a portion of the cutter sheath resists movement by the abrading blade to increase a current blade angle for the abrading blade positioned within the sheath slot;
    wherein the sheath slot is comprised of
        an axial slot open at a distal end of the cutter sheath; and
        a radial slot open to the axial slot.

\* \* \* \* \*